(12) United States Patent
Gomez et al.

(10) Patent No.: US 7,306,924 B2
(45) Date of Patent: *Dec. 11, 2007

(54) BIOSENSOR AND RELATED METHOD

(75) Inventors: Rafael Gomez, West Lafayette, IN (US); Rashid Bashir, West Lafayette, IN (US); Arun K. Bhunia, West Lafayette, IN (US); Michael R. Ladisch, West Lafayette, IN (US); J. Paul Robinson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 476 days.

This patent is subject to a terminal disclaimer.

(21) Appl. No.: 10/184,237

(22) Filed: Jun. 26, 2002

(65) Prior Publication Data

US 2003/0157587 A1  Aug. 21, 2003

Related U.S. Application Data

(63) Continuation-in-part of application No. 09/817,541, filed on Mar. 26, 2001, now Pat. No. 6,716,620.

(60) Provisional application No. 60/197,560, filed on Apr. 17, 2000.

(51) Int. Cl.
*G01N 33/569* (2006.01)
*C12Q 1/04* (2006.01)

(52) U.S. Cl. .................... 435/7.2; 435/30; 435/34; 435/173.9; 435/287.1; 435/287.2; 435/288.5; 204/547; 204/643

(58) Field of Classification Search .................. 435/4, 435/6, 7.2, 288.6, 288.7, 287.2, 288.4, 288.5, 435/817, 287.1; 204/452, 453, 603, 604, 204/403, 466, 547, 616, 643; 422/58, 68.1, 422/100, 101, 102, 82.02; 324/444, 439, 324/445, 446, 450, 692; 436/63
See application file for complete search history.

(56) References Cited

U.S. PATENT DOCUMENTS 3,676,775 A  7/1972  Dupnock et al.

(Continued)

FOREIGN PATENT DOCUMENTS

| GB | 2358473 A | * | 7/2001 |
| GB | 2361883 A | * | 11/2001 |
| WO | WO 200105511 A1 | * | 1/2001 |

OTHER PUBLICATIONS

Database Derwent, Accession No. 1986-050505, of JP 61002060 A, Matsushita Electric Works Ltd, Jan. 8, 1986.

(Continued)

*Primary Examiner*—William H. Beisner
(74) *Attorney, Agent, or Firm*—R. Neil Sudol; Henry D. Coleman; William J. Sapone

(57) ABSTRACT

A method for collecting a microbiological substance utilizes a micro fabricated biochip having a collection chamber. A fluid sample containing a microbiological entity of interest is delivered to the collection chamber in the biochip. Then a non-uniform electric field is generated in the collection chamber, to retain the microbiological entity of interest in the collection chamber. The microbiological entity is retained through dielectrophoresis induced by the energization of the electrodes by a periodically applied, alternating current.

14 Claims, 16 Drawing Sheets

U.S. PATENT DOCUMENTS

| | | | |
|---|---|---|---|
| 3,984,766 A | 10/1976 | Thornton | |
| 4,009,078 A | 2/1977 | Wilkins et al. | |
| 4,072,578 A | 2/1978 | Cady et al. | |
| 4,156,180 A | 5/1979 | Annen et al. | |
| 4,160,205 A | 7/1979 | Hobbs et al. | |
| 5,187,096 A | 2/1993 | Giaever et al. | |
| 5,192,507 A | 3/1993 | Taylor et al. | |
| 5,432,086 A | 7/1995 | Franzl et al. | |
| 5,571,410 A | 11/1996 | Swedberg et al. | |
| 5,593,838 A | 1/1997 | Zanzucchi et al. | |
| 5,643,742 A | 7/1997 | Malin et al. | |
| 5,670,031 A | 9/1997 | Hintsche et al. | |
| 5,726,026 A | 3/1998 | Wilding et al. | |
| 5,789,191 A | 8/1998 | Mayer et al. | |
| 5,824,494 A | 10/1998 | Feldberg | |
| 5,837,196 A | 11/1998 | Pinkel et al. | |
| 5,954,931 A | 9/1999 | Maracas et al. | |
| 5,981,268 A | 11/1999 | Kovacs et al. | |
| 6,007,690 A | 12/1999 | Nelson et al. | |
| 6,051,422 A | 4/2000 | Kovacs et al. | |
| 6,130,037 A | 10/2000 | Lennox et al. | |
| 6,143,247 A | 11/2000 | Sheppard et al. | |
| 6,149,787 A | 11/2000 | Chow et al. | |
| 6,165,335 A | 12/2000 | Lennox et al. | |
| 6,169,394 B1 | 1/2001 | Frazier et al. | |
| 6,300,141 B1 | 10/2001 | Segal et al. | |
| 6,319,469 B1 | 11/2001 | Mian et al. | |
| 6,416,642 B1 | 7/2002 | Alajoki et al. | |
| 6,576,459 B2 * | 6/2003 | Miles et al. | 435/286.5 |
| 6,716,620 B2 * | 4/2004 | Bashir et al. | 435/287.2 |
| 6,764,583 B2 * | 7/2004 | Miles | 204/452 |
| 6,835,552 B2 * | 12/2004 | Miles et al. | 435/7.32 |
| 2002/0076825 A1 * | 6/2002 | Cheng et al. | 436/174 |

OTHER PUBLICATIONS

Database Derwent, Accession No. 1999-561516, of AU 9926381, Loessner, M J. et al., Bioseng Technologies Ltd, Sep. 20, 1999.

Biosensors & Bioelectronics, 12 No. 9-10 pp. 977-989, 1997, V.M.Mirsky, M. Riepl, & O.S. Wolfbeis.

Biophysical Chemistry, vol. 62 pp. 63-72, 1996, Nakata, Kido, Hayashi, Hara, Sasabe, Sugawara, Matsuda.

Biotechnol. Prog., No. 15 pp. 991-1002, 1999, Itamar Willner, Bilha Willner.

Journal of Colloid & Interface Science, 164 pp. 181-189, 1994, Razumas, Nylander, Arnebrant.

Proc. Natl. Acad. Sci. USA, 93 pp. 12287-12291, 1996, Mooney, Hunt, McIntosh, Liberko, Walba, Rogers.

Biotechnol. Prog., vol. 8 No. 2 pp. 155-160, 1992, Britland, Perez-Arnaud, Clark, McGinn, Connolly, Moores.

Analytical Chemistry, vol. 71, No. 15, pp. 3110-3117, 1999, Morozov, Morozova.

Purdue University Grad School Thesis, Form No. 9-36667, 1988, Stephen J. Duey.

Sensors and Actuators, B33 pp. 105-109, 1996, Harrison, Fluri, Chiem, Tang, Fan.

Sensors and Actuators, B44 pp. 578-584, 1997, Berney, Alderman, Lane, Collins.

Journal of AOAC International, vol. 75, No. 2 pp. 293-302, 1992, Gibson, Coombs, Pimbley.

Analytica Chimica, vol. 289 pp. 321-327, 1994, Hoshi, Anzai, Osa.

Analytica Chimica, vol. 392 pp. 77-84, 1999, Riepl, Mirsky, Novotny, Tvarozek, Rehacek, Wolfbeis.

Fresenius J Anal. Chem., vol. 366 pp. 622-634, 2000, Warsinke, Benkert, Scheller.

Talanta, vol. 44 pp. 2003-2010, 1997, Wang, Rivas, Parrado, Cai, Flair.

Analytical Chemistry, vol. 70 No. 17 pp. 3674-3678, 1998, Mirsky, Mass, Krause, Wolfbeis.

Analytical Chemistry, vol. 67 No. 20 pp. 3676-3680, 1995, Woolley, Mathies.

Journal of Food Protection, vol. 63 No. 2 pp. 264-267, 2000, Edmiston, Russell.

Journal of Food Protection, vol. 62 No. 12 pp. 1488-1496, 1999, Wawerla, Stolle, Schalch, Eisgruber.

Journal of Microbiological Methods, vol. 35 pp. 37-42, 1999, Felice, Madrid, Olivera, Rotger, Valentinuzzi.

Sensors and Actuators, B43 pp. 121-125, 1997, Jobst, Moster, Svasek, Varahram, Trajanoski, Wach, Kotanko, Skrabal, Urban.

Sensors and Actuators, B49 pp. 73-80, 1998, Gerwen, Laureyn, Laureys, Mertens, Huyberechts, Baert, Sansen, De Beeck, Jacobs, Hermans, Suls.

Sensors and Actuators, B47 pp. 225-230, 1998, Schöning, Thust, Müller-Veggian, Kordoš, Lüth.

Biosensors & Bioelectronics, vol. 10 pp. 675-682, 1995, DeSilva, Zhang, Hesketh, Maclay, Gendel, Stetter.

Biosensors & Bioelectronics, vol. 13 pp. 1061-1068, 1998, Berggren, Bjarnason, Johansson.

Biosensors & Bioelectronics, vol. 12 No. 1 pp. 29-41, 1997, Ehret, Baumann, Brischwein, Wolf, Schwinde, Stegbauer.

IEEE Engineering in Medicine & Biology, Mar./Apr. 1996 pp. 100-103, Michael J. Heller.

Biosensors & Bioelectronics, vol. 12 No. 9-10 pp. 893-899, 1997, Towe, Pizziconi.

John Wiley & Sons, Inc. School of Mechanical Engineering, Purdue University, Intro. To Fluid Mech. Fifth Edition, 1998, Fox, McDonald.

Experiments in Fluids, vol. 27 pp. 414-419, 1999, Meinhart, Wereley, Santiago.

"Microfluidic Biochip for Impedance Spectroscopy of Biological Species"; R. Gomez, R. Bashir, A. Sarikaya, M.R. Ladisch, J. Sturgis, J.P. Robinson, T. Geng, A.K. Bhunia, H.L. Apple & S. Wereley; 2001; pp. 201-209.

"Impedance based sensing of the specific binding reaction between *Staphylococcus* enterotoxin B and its antibody on an ultra-thin platinum film"; M. DeSilva, Y. Zhang, P. Hesketh, G. Maclay, S. Gendel & J. Stetter; 1995; pp. 675-682.

"Immunosensors: electrochemical sensing and other engineering approaches"; A. Ghindilis, P. Atanasov, M. Wilkins & E. Wilkins; 1998; pp. 113-131.

* cited by examiner

BIOSENSOR AND RELATED METHOD

CROSS-REFERENCE TO A RELATED APPLICATIONS

This application is a continuation-in-part of application Ser. No. 09/817,541 filed Mar. 26, 2001 now U.S. Pat. No. 6,716,620. That prior application in turn relies for priority purposes on U.S. provisional application No. 60/197,560 filed Apr. 17, 2000.

STATEMENT REGARDING FEDERALLY SPONSORED RESEARCH

This invention and/or underlying inventions were made with Government support under a USDA cooperative agreement: CRIS number 1935-42000-035-00D, Agreement # 58-1935-9-010. This invention was also partially funded through a NSF IGERT graduate student fellowship. The Government has certain rights in the invention.

BACKGROUND OF THE INVENTION

The present invention relates to an integrated-chip-type biosensor and a related method for detection of pathogenic substances. The biosensor and method are particularly, but not exclusively, useful in detecting foodborne pathogens such as *Listeria monocytogenes*.

Pathogenic bacteria in foods are the cause of 90% of the cases of reported foodborne illnesses. The Centers for Disease Control and Prevention estimate that there 76 million cases of foodborne illnesses each year in the United States, resulting in hospitalization of 325,000 people, 5,500 deaths, and an annular cost of $7 to $23 billion. *E. coli* O157:H7 and *Listeria monocytogenes* are the pathogens of most concern. Ground meat containing *E. coli* O157:H7 is now considered to be an adulterated food while *Listeria monocytogenes* has emerged as one of the most important food pathogens with a "zero tolerance" criterion for it in ready-to-eat processed (lunch) meats and dairy foods.

The genus *Listeria* is comprised of six species, *L. monocytogenes, L. ivanovii, L. seeligeri, L. innocua, L. welshimeri*, and *L. grayi*. Of these species, only *L. monocytogenes* is harmful to humans. Consumption of contaminated food may cause meningitis, encephalitis, liver abscess, headache, fever and gastroenteritis (diarrhea) in immunologically challenged individuals and abortion in pregnant women. *L. monocytogenes* is ubiquitous in nature and can be found in meat, poultry, seafood, and vegetables. Occurrence of this organism could be as high as 32%. In a food sample, *L. monocytogenes* is often present in close association with other nonpathogenic *Listeria* species, thereby complicating the specific detection procedures. A successful detection method ideally detects only *L. monocytogenes* in the presence of overwhelming populations of nonpathogenic *Listeria* and other background resident bacteria.

The food processing industry annually carries out more than 144 million microbial tests costing $5 to $10 each. About 24 million of these tests are for detection of food pathogens based on biochemical profile analysis, immunogenic tests (such as enzyme linked immuno-sorbent assays or ELISA), and DNA/RNA probes. These tests are reliable but most require two to seven days to complete because of the steps that are needed to resuscitate cells, increase cell numbers or amplify genetic material needed for detection. This time period is too long for real-time detection of contamination in a food plant and is sufficiently long for contaminated food to be formulated, processed, packaged, shipped, and purchased and eaten by the consumer. Current tests require at least several days to confirm presence of *Listeria monocytogenes*. The number of annual tests is only expected to increase due to heightened consumer concerns about food safety and the requirement of compulsory testing.

In general, diagnostic tools used for detecting or quantitating biological analytes rely on ligand-specific binding between a ligand and a receptor. Ligand/receptor binding pairs used commonly in diagnostics include antigen-antibody, hormone-receptor, drug-receptor, cell surface antigen-lectin, biotin-avidin, substrate/enzyme, and complementary nucleic acid strands. The analyte to be detected may be either member of the binding pair; alternatively, the analyte may be a ligand analog that competes with the ligand for binding to the complement receptor.

A variety of devices for detecting ligand/receptor interactions are known. The most basic of these are purely chemical/enzymatic assays in which the presence or amount of analyte is detected by measuring or quantitating a detectable reaction product, such as a detectable marker or reporter molecule or ligand. Ligand/receptor interactions can also be detected and quantitated by radiolabel assays.

Quantitative binding assays of this type involve two separate components: a reaction substrate, e.g., a solid-phase test strip and a separate reader or detector device, such as a scintillation counter or spectrophotometer. The substrate is generally unsuited to multiple assays, or to miniaturization, for handling multiple analyte assays from a small amount of body-fluid sample.

In recent years, there has been a merger of microelectronics and biological sciences to develop what are called "biochips." The term "biochip" has been used in various contexts but can be defined as a "micro fabricated device that is used for delivery, processing, and analysis of biological species (molecules, cells, etc.)." Such devices have been used, among other things, for the direct interrogation of the electric properties and behavior of cells (Borkholder et al. "Planar Electrode Array Systems for Neural Recording and Impedance Measurements", *IEEE Journal of Microelectromechanical Systems*, vol 8(1), pp. 50-57, 1999); impedance-based detection of protein binding to surfaces, antigen-antibody binding, and DNA hybridization (DeSilva et al., "Impedance Based Sensing of the Specific Binding Reaction Staphylococcus Enterotoxin B and its Antibody on an Ultrathin Platinum Film," *Biosensors & Bioelectronics*, vol. B 44, pp 578-584, 1995); micro-scale capillary electrophoresis (Wooley et al., :Ultra High Speed DNA Sequencing Using Capillary Electrophoresis Chips," *Analytical Chemistry*, vol. 67(20), pp. 3676-3680, 1995); and optical detection of DNA hybridization using fluorescence signals in the commercially available "DNA-chips" (Fodor et al., "Light-directed Spatially Addressable Parallel Chemical Synthesis," *Science*, vol. 251, pp. 767-773).

One of the most interesting uses of biochips is for the detection of small quantities of pathogenic bacteria or toxigenic substances in food, bodily fluids, tissue samples, soil, etc. In applications such as the screening of food products for the presence of pathogenic bacteria, it would be beneficial to detect between 100 and 1000 microorganisms per milliliter of sample, with a sample volume of a couple of milliliters. Not counting the fact that bacteria are substantially larger than single biomolecules (~2 μm vs. ~10-100 Å), 1000 cells are approximately equivalent to a $10^{-5}$ femtomoles of cells, which gives an idea of the difficulty in directly detecting such a small number suspended in a volume of 1 or 2 ml, along with large numbers of food debris, proteins, carbohydrates, oils, and other bacteria. Additionally, in many cases the screening technique must be able to discern between viable and dead cells. Many bacteria will not produce toxins when not viable and consequently will not be pathogenic in that state. DNA detection methods, which search for DNA sequences specific to the pathogen of interest, can be extremely sensitive because they rely on the very specific binding of complementary DNA strands, often coupled with Polymerase Chain Reaction (PCR) for amplification. But the detected DNA fragments cannot reveal whether the pathogen was viable or not. These are the main reasons why current methods of detection almost always involve a growth step, in which the bacteria are cultured to increase their numbers by several orders of magnitude. Once the bacteria are amplified to a large number, visual detection of colonies or Enzyme-Linked Immunosorbent Assays (ELISA) confirm their presence in the original sample. Even though bacteria can multiply very rapidly, this amplification by means of extended growth makes conventional detection methods extremely lengthy, taking anywhere from 2 to 7 days. Thus, one of the main goals of micro-scale detection is a reduced time of analysis, on the order of 2 to 4 hours, to be better than the more conventional methods like plate counts and ELISA.

Numerous reports can be found in the literature on biosensors based on the impedimetric detection of biological binding events, or the amperometric detection of enzymatic reactions. (See DeSilva et al., "Impedance Based Sensing of the Specific Binding Reaction Staphylococcus Enterotoxin B and its Antibody on an Ultra-thin Platinum Film," *Biosensors & Bioelectronics*, vol. B 44, pp 578-584, 1995; Mirsky et al., "Capacitive Monitoring of Protein Immobilization and Antigen-antibody Reactions on Monomolecular Alkylthiol films on Gold Electrodes," *Biosensors & Bioelectronics*, vol. 112(9-10), pp. 977-989, 1997; Berggren et al., "An Immunilogical Interleukine-6 Capacitive Biosensor Using Perturbation with a Potentiostatic Step," *Biosensors & Bioelectronics*, vol. 13, pp. 1061-1068, 1998; Van Gerwen et al., "Nanoscaled Impedimetric Sensors for Multiparameter Testing of Biochemical Samples," *Sensors and Actuators*, vol. B 49, pp. 73-80, 1998; Hoshi et al., "Electrochemical Deposition of Avidin on the Surface of a Platinum Electrode for Enzyme Sensor Applications," *Analytical Chimica Acta*, vol. 289, pp. 321-327, 1994; Jobst et al., "Mass producible Miniaturized Flow Through a Device with a Biosensor Array," *Sensors and Actuators*, vol. B 43, pp. 121-125, 1997; Towe et al., "A Microflow Amperometric Glucose Biosensor," *Biosensors & Bioelectronics*, vol. 97(9), pp. 893-899, 1997.) Impedimetric detection works by measuring impedance changes produced by the binding of target molecules to receptors (antibodies, for example) immobilized on the surface of microelectrodes. Amperometric devices measure the current generated by electrochemical reactions at the surfaces of microelectrodes, which are commonly coated with enzymes. Both of these methods can be very sensitive, but preparation of the surfaces of the electrodes (immobilization of antibodies or enzymes) is a complex and sometimes unreliable process, they can be prone to drift, and tend to be very sensitive to noise produced by the multitude of species present in real samples (bodily fluids, food, soil, etc.).

Most, if not all, of the above-mentioned devices are not fully integrated biochips, and sometimes lack integrated electrodes and a sealed fluidic path for the injection and extraction of samples. The most common design of these sensors uses thin metal rods or wires as electrodes, immersed in a flow-through cell. And even those devices based on micro fabricated biochips either have a fluidic system separately fabricated over the chip, or the samples are dropped over an open reservoir on the chip, or the whole chip is immersed in a vessel containing the fluids. Having a fully closed system permits the incorporation of sample pre-processing steps, like filtering and chromatography, onto the same chip as the detector.

As mentioned earlier, one of the main goals of bacterial sensors is to determine whether the bacterium of interest is indeed live or dead. A technique that has been widely reported to detect the viability of bacteria on a macro-scale relies on measuring the conductance/impedance changes of a medium in which the microbes are cultured. Such a method is recognized by the Association of Official Analytical Chemists International (AOAC) as a standard technique for the detection of Salmonella in food. This is possible because bacterial metabolism changes the electrolyte concentration in the suspension medium, significantly altering the electrical characteristics of the medium.

OBJECTS OF THE INVENTION

It is a general object of the present invention to provide a method and/or an associated apparatus for facilitaqting the collection of a microbiological substance or entity such as a microorganism.

A related general object of th present invention is to provide a method and/or associated apparatus for detecting whether a microbiological substance (e.g., microorganism) is present in a fluid sample.

A more specific object of the present invention is to provide a method and/or an associated device for use in a more rapid process for detecting foodborne pathogens, particularly including, but not necessarily limited to, *Listeria monocytogenes*.

An even more specific object of the present invention is to provide such a method and/or device which facilitates the collection and detection of pathogens in a few hours or less, possibly within minutes.

A further specific object of the present invention is to provide a method and/or device which is useful in detecting a relatively small number of instances of a pathogen such as a bacterium.

These and other objects of the present invention will be apparent from the drawings and descriptions herein. Every object of the invention is attained by at least one embodiment of the invention. However, no embodiment necessarily meets every object set forth herein.

SUMMARY OF THE INVENTION

The present invention is directed in part to a microscale biochip for use particularly in the detection of target biological substances including molecules and living cells. A preferred embodiment of a biochip pursuant to the present invention is a microfluidic system with integrated electronics, inlet-outlet ports and interface schemes, high sensitivity detection of pathogen specificity, and processing of biological materials at semiconductor interfaces.

More specifically, the present invention is directed to that portion of an integrated biosensor used for collecting a target microbiological entity. The present invention is concomitantly directed to a method of collecting microbiological entities of interest.

A method for collecting a microbiological substance comprises, in accordance with the present invention, providing a micro fabricated biochip having a collection chamber, delivering to the collection chamber in the biochip a fluid sample containing a microbiological entity of interest, generating a non-uniform electric field in the collection chamber, and retaining the microbiological entity of interest in the collection chamber by virtue of the non-uniform electric field. The non-uniform electric field enables a process known as dielectrophoresis by which a retaining force is exerted on certain particles.

Pursuant to another feature of the present invention, the non-uniform electric field is applied periodically, in a pulsed mode. The microbiological entity of interest is attached to the collection chamber (e.g., to the walls thereof, or to electrodes disposed in the collection chamber, via antibodies and/or by carrier elements such as microspheres) during intervals of application of the non-uniform electric field. At least some contaminants are removed from the fluid sample in the collection chamber during periods between successive intervals of application of the non-uniform electric field. This removal is effectuated by flowing the fluid sample through and out of the chamber.

After the removing of contaminants from the fluid sample, detection elements in the collection chamber may be operated to determine whether the fluid sample contains the microbiological entity of interest. The detection elements may be electrodes for measuring the conductivity of the liquid of the fluid sample. Where the microbiological entity of interest is a microorganism, the temperature of the fluid sample is controlled and a nutrient is provided which is utilizable by the microbiological. Thus, if the microorganism is alive, metabolic activity will produce ionic byproducts that will alter the conductivity or other electrical parameter of the fluid sample.

The present invention contemplates that contaminants are separated from the fluid sample in the collection chamber by trapping carrier elements with the coupled microbiological entity of interest in the collection chamber and flushing remaining portions of the fluid sample from the collection chamber.

The collection method of the present invention is particularly useful where the microbiological entity of interest is a pathogenic strain of bacteria. For example, where the pathogenic strain of bacteria is *Listeria monocytogenes*, the fluid sample may be extracted from a food product prior to delivering of the fluid sample to the biochip. Pursuant to another feature of the present invention, the method may further comprise measuring an electrical parameter of fluid in the collection chamber to detect metabolic activity of the microbiological entity of interest, thereby determining viability of the microbiological entity of interest.

A biochip comprises a substrate micro fabricated to include, as integrated components, a collection chamber, a first channel segment extending to an inlet of the collection chamber, a second channel segment extending from an outlet of the chamber, and a retention structure for holding, in the chamber, carrier elements entraining a target microbiological species while permitting passage through the collection chamber of contaminant materials in a fluid stream, the retention structure including electrodes for generating a non-uniform electric field. The electrodes typically have differing geometries to generate a non-uniform field.

A method for collecting a microorganism comprises, in accordance with another embodiment of the present invention, preparing a fluid sample containing at least one microorganism of a preselected type, delivering the fluid sample to a collection chamber having a volume less than approximately 1 microliter, and retaining the microorganism in the collection chamber by dielectrophoresis. The preparing of the fluid sample may include attaching the microorganism to carrier elements, while the retaining of the microorganism in the collection chamber includes retaining the carrier elements therein. The method may additionally include a step of measuring an electrical parameter (phase, magnitude, etc.) of an electrical circuit incorporating the collection chamber and the fluid sample therein. The measurement is usd to determine whether the microorganism in the collection chamber is alive and producing metabolites.

A microfluidic biochip used for impedance spectroscopy of biological species and including the collecting apparatus of the present invention is preferably fabricated by an all top-side processing for the formation of fluidic channels, planar fluidic interface ports, integrated metal electrodes for impedance measurements and non-uniform-electric-field generation. A glass cover may be used to seal the non-planar topography of the chip using spin-on-glass as an intermediate bonding layer. In one embodiment of the biochip, the total volume of the fluidic path in the device is on the order of 30 nl.

A method in accordance with the present invention for collecting and optionally detecting a microbiological substance utilizes a micro fabricated biochip including integrated collection and detection elements. The method in part comprises delivering a fluid sample to the biochip and thereafter separating at least some contaminants or debris from the fluid sample to at least partially isolate and retain instances of a predetermined target type of microbiological material, a material to be detected, on the biochip. Thus, the separating of the contaminants takes place at least in part on the biochip itself. After the separating of contaminants from the fluid sample, detection elements may be operated to determine whether the separated fluid sample contains microbiological material of the predetermined target type (e.g., living pathogenic bacteria).

This method may further comprise carrying out a bioseparations process on the fluid sample prior to the delivering of the fluid sample to the biochip. In that case, the bioseparations process may include adding to the fluid sample a plurality of microscopic carrier elements each provided with a multiplicity of binding agents for coupling the microbiological material (e.g., microorganisms) to the carrier elements. These carrier elements preferably take the form of beads or microspheres. The separating of contaminants from the fluid sample on the biochip preferably includes trapping the carrier elements with the coupled microbiological material in a collection/detection chamber on the biochip while flushing remaining portions of the fluid sample from the chamber. This trapping of the carrier elements with the coupled microbiological material in a detection chamber serves in part to concentrate the microbiological material of interest and thus enhance the sensitivity of the detection technique. The trapping of the carrier elements is implemented in accordance with the present invention by a dielectrophoresis process implemented with electrodes of different geometries.

The present invention is especially useful in detecting pathogenic strains of bacteria. In that case, the methodology includes extracting the fluid sample from a food product prior to delivering of the fluid sample to the biochip. As discussed below, the collection of the pathogenic bacteria is implemented in part by attaching antibodies to a capture surface in the collection/detection chamber of the biochip. That capture surface may be on an electrode or oxide surface in the detection chamber. Alternatively, the capture surface may be on a bead or microsphere floating in the detection chamber. It will be apparent to one of ordinary skill in the art that virtually any microorganism may be detected by the method of the present invention simply by attaching an appropriate antibody to a capture surface as described herein. Antibodies and their associated antigens on the cell membranes of various microorganisms are well documented in the art. It will also be apparent to one skilled in the art that species other than bacteria may be detected by the methodology of the present invention. Various proteins, peptide groups, nucleic acid chains, and other molecules may be detected by the selection of suitable binding agents and the attachment of those binding agents to a capture surface in a detection chamber of a biochip.

A biochip in accordance with the present invention comprises a substrate micro fabricated to include, as integrated components, a collection/detection chamber, a first channel segment extending to an inlet of the collection/detection chamber, a second channel segment extending from an outlet of the chamber, and dielectrophoresis electrodes for holding, in the collection/detection chamber, a carrier element entraining a target microbiological species and for permitting the passage from the collection/detection chamber of contaminants or debris in a fluid sample containing the carrier element and the target microbiological species.

The retention structure (electrodes) on the biochip enables the concentration of a target microbiological species at the point of measurement. This facilitates and enhances the detection process. The small size of the detection chamber, less than 100 microliters and preferably between about 1 picoliter and 1 microliter, also increases the sensitivity of the detection process. Yet another factor contributing to the efficacy of the present methodology is the use of a low or medium conductivity buffer as the fluid matrix in which the microbiological species of interest is entrained in the detection chamber.

The electrophoresis or collection electrodes may also be used for carrying out the detection process. Alternatively, a separate set of electrodes, preferably with interdigitated finger parts, may be provided for measurement purposes. The volume of a fluid sample in the device may be substantially less than one microliter, even down to about 1 picoliter. The electrodes are spaced from each other by 1 to 100 microns and, more preferably, by 2 to 50 microns.

A biochip in accordance with another embodiment of the present invention may include a wicking element connected at one end to the biochip substrate so as to be in communication with an inlet channel, for drawing a fluid sample by capillary action to the channel for delivery to the collection/detection chamber. The wicking element may be attached at the one end by an adhesive to the substrate. Where the substrate is micro fabricated to include an inlet groove or trench substantially coplanar with the channel and the detection chamber, the one end of the wicking element is disposed in the inlet groove or trench, so that the wicking element is coplanar at the one end with the channel and the detection chamber.

Preferably a boichip in accordance with the present invention is top-side processed only. In addition, there is no processing (e.g., cutting) of a cover plate. This structure facilitates the manufacturing process, in part by obviating alignment requirements between the cover plate and the substrate. Thus, the cover attached to the substrate over the detection chamber, the channel, the inlet groove, and the downstream end of the fluid delivery member can be an integral or continuous member, devoid of holes or apertures. Such holes or apertures would be required, for instance, where a feed tube was to be inserted through the cover.

In a method for detecting a microorganism in accordance with the present invention, a fluid sample is maintained at a predetermined temperature in a detection chamber and an electrical parameter of an electrical circuit incorporating the detection chamber and the fluid sample therein is measured. The electrical parameter is an impedance measure taken from the group consisting of a magnitude and phase. The measuring of the electrical parameter may include measuring the impedance parameter at a plurality of frequencies within a range from 100 Hz to 1 MHz.

The sensitivity to biological pathogens of a boichip in accordance with the present invention is based on the placement of protein receptors, derived through biotechnology processes, on a surface of the biochip. A tiny amount of fluid taken from a specimen such as a processed meat or dairy product is then delivered to the biochip. If a target bacterium such as *Listeria monocytogenes* is present, it will bind to the receptor and cause a measurable electronic signal to be generated in no more than several hours and possibly within minutes.

The present invention provides a method and an associated device for the relatively rapid detection of biological pathogens such as bacteria. The method and device can detect small numbers of bacteria such as *Listeria monocytogenes* in time intervals short enough to enable removal of contaminated products from the stream of commerce before consumption of the products by individuals.

Biochips or biochips as disclosed herein improve the quality of life by providing cost-effective means for probing biological materials for pathogenic organisms and molecules in manufacturing facilities, the environment, hospitals, doctors' offices, and ultimately in the home.

The present invention provides a method and an associated device for a relatively rapid detection of foodborne pathogens. The present invention obviates the time-consuming steps of culturing and transferring cells, if present, to increase their numbers or genetic material to the detectible levels required by conventional detection techniques.

The vast majority of the bacterial detection methods currently in use are based on fluorescent tagging of the bacteria, or on the detection of DNA fragments from the bacterial genome. Both techniques are unable to determine if the microorganism was dead or alive in the original sample, and both require extensive manipulations of the sample. Moreover, any fluorescence technique requires bulky and expensive optical apparatuses for excitation and detection of the fluorescence. Additionally, when the microorganism is present in very small concentrations (10 to 1000 cells per milliliter) a growth step is necessary to increase the concentration, but this can drive the total assay time to anywhere from 2 to 7 days.

The present technique solves some of these problems. By its very nature, the present methodology inherently detects only live microorganisms, which is very important for certain applications, especially in food safety (many microorganisms present in food are not pathogenic if they are dead). The method of the present invention also relies exclusively on electrical signals, making the related equipment less expensive and smaller than others. Additionally, the absence of a lengthy growth step makes detection possible in a couple of hours instead of days.

Instruments for the analysis of the conductivity or impedance of an incubated bacterial suspension have been available for a number of years, but they suffer from two limitations. First, their selectivity is very poor because they rely on the composition of the growth medium for encouraging the proliferation of the microorganism of interest, while suppressing the proliferation of others. The second limitation is related to the scale in which the assay is performed. The available equipment uses volumes of bacterial suspension in the milliliter range and above, which requires large numbers of bacteria to provide a discernible signal. The method of the present invention eliminates the first limitation by selectively capturing the bacteria using antibodies prior to the measurement, and increases the sensitivity for very small numbers of microorganisms (1 to 1000) by confining them to an extremely small volume (1 picoliter to 1 microliter). Additionally, the method of the present invention uses a low conductivity buffer, which increases even further the sensitivity. Even very small amounts of ions released by the microorganisms can produce a large change in impedance (in relative terms), since the ionic concentration of the low conductivity buffer is very low.

DEFINITIONS

Figure 1:
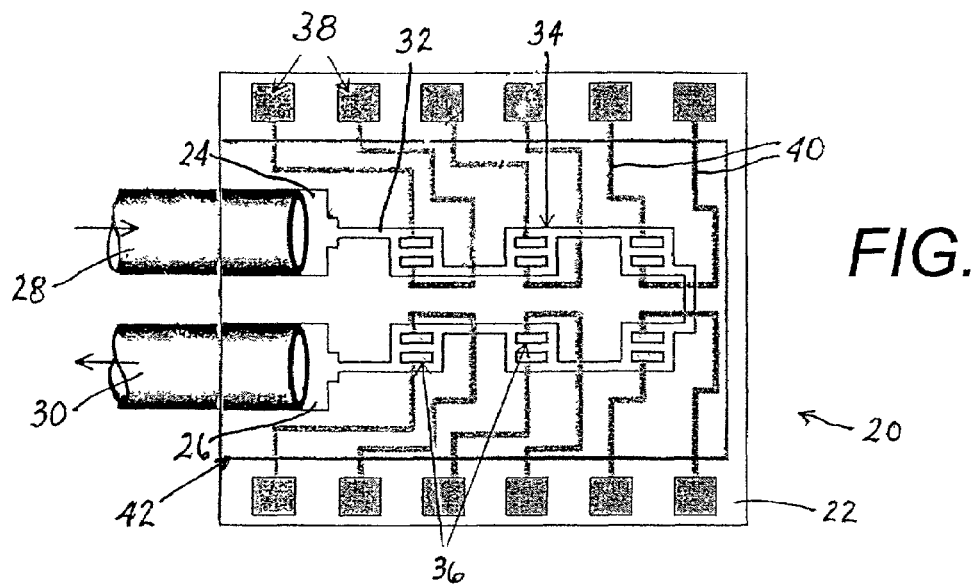
FIG. 1 is a schematic top plan view of a biosensor in accordance with the present invention.

Avidin is a protein with four identical subunits and a total molecular weight of 67,000-68,000 daltons. Biotin is a vitamin (B-6) having a molecular weight of 244 daltons. Each subunit of an avidin molecule binds one molecule of biotin. The binding action is pronounced: affinity of biotin to avidin is very strong ($K_a=10^{15}$ $M^{-1}$). The avidin-biotin system is well-established and extensively used as a biological probe.

The word "biotinylated" is used herein to generically describe a preselected molecule, generally a protein, which has been derivatized with biotin. Where avidin has been adsorbed to a capture surface such as a surface of an electrode in a detection chamber, the biotin functions to secure the preselected molecule to the capture surface via the avidin-biotin linkage.

The term "binding agent" is used herein to denote a chemical structure such as an antibody or a molecular complex (two or more molecules coupled together) capable of latching onto or capturing a target microbiological species or material which is to be detected in a biochip sensor pursuant to the techniques described herein. A biotinylated antibody bound to avidin on a capture surface of an electrode serves as a binding agent for a target bacterium having a cell membrane carrying the antigen of the biotinylated antibody.

The terms "biosensor" and "biochip" as used herein refer to microelectronic-inspired construction of devices that are used for processing (delivery, analysis or detection) of biological molecules and cellular species. Thus, a biosensor or boichip as described herein is a microfluidic system with integrated electronics, inlet-outlet ports and interface schemes, high sensitivity detection of pathogen specificity, and processing of biological materials at semiconductor interfaces.

The word "bioseparation" or "bioseparations" as used herein refers to a process for removing contaminants and detritus from a fluid sample possibly containing a target microbiological species.

The term "capture surface" as used herein refers to a surface in a boichip sensor or in a preseparation process which is prepared with a binding agent for purposes of latching onto and holding, at least for the duration of a detection process, a target substance, whether that target consists of a molecule such as a protein, an antibodies, an antigens, or an enzyme; a molecular fragment such as a peptide or a DNA sequence; or a cell such as a muscle cell or a bacterium; a virus; etc.

The word "carrier" as used herein refers to movable structures to which binding agents are attached for securing, anchoring or attaching target microbiological materials. One kind of carrier is a microsphere or bead made of magnetic or nonmagnetic material.

The words "contaminants" and "detritus" are used herein to describe various microscopic and submicroscopic cells, cellular fragments, molecules, molecular fragments, which are of no interest to a biosensor detection process in accordance with the present invention. Contaminants can be disruptive of the detection process, for example, by causing noise to electrical detection.

The term "detection chamber" is used herein to generally designate a space provided with sensors for measuring a change in a predetermined parameter owing to the presence of a target microbiological species in the detection chamber. In a more specific embodiment of the invention, the term "detection chamber" is used to designate a small well or cavity produced by microfabrication techniques in a wafer and provided with sensing elements such as electrodes for sensing a change in an electrical characteristic or parameter (such as resistance or phase) in the chamber owing to the presence of the target microbiological species. This specific detection chamber has a small volume, no more than 100 microliters, and preferably no more than 1 microliter, and even more preferably, in a range about 1 to 10 nanoliters.

The term "low conductivity" is used herein with reference to a buffer solution which has a sufficiently low concentration of charge carriers (e.g., ions) to enable detection of a difference in an impedance parameter, such as magnitude or phase, between a bacteria-containing sample and a reference sample free of bacteria.

The term "microbiological species" or "microbiological material" is used herein to denote any microscopic or submicroscopic entity of interest to researchers or commerce. The term encompasses molecules such as proteins, antibodies, antigens, and enzymes; molecular fragments such as peptides and DNA sequences; cells such as muscle cells or bacteria; viruses; fungi; etc.

The word "micro fabricated" or "microfabrication" as used herein refers to the utilization of photolithography, X-ray lithography, acid etching, and other silicon treatment processes developed in the semiconductor industry to manufacture integrated circuits and solid state components such as microprocessor chips.

The term "target" is used herein to mean a microbiological entity or species of interest. A target microbiological species is that which is to be detected by a biosensor or boichip as herein described.

The term "wicking element" as used herein denotes any elongate guide capable of moving a liquid sample by capillary action, where the liquid sample include molecular and cellular material.

The term "dielectrophoresis" is used herein to denote a process of transporting particles in a non-uniform electric field. Such a field is generated by electrodes of different geometries, for instance, a negative electrode in the form of a large plate and a positive electrode in the form of a small plate or finger. In this case, the direction of the force on a particle, towards the positive or negative electrode, depends on whether the particle is more polarizable or less polarizable than the surrounding fluid medium.

The term "collection chamber" is used herein to generally designate a microscopic or submicroscopic space provided with micro fabricated parts for performing a filtration or selective concentration process to retain a target microbiological species in the collection chamber. In a more specific embodiment of the invention, the term "collection chamber" is used to designate a small well or cavity produced by microfabrication techniques in a wafer and provided with micro fabricated elements such as electrodes for generating a capture field in the chamber. This specific collection chamber has a small volume, no more than 100 microliters, and preferably no more than 1 microliter, and even more preferably, in a range about 1 to 10 nanoliters. A collection chamber may include measurement or sensing components as discussed above with respect to the term "detection chamber." The measurement components may be different from or the same as the collection components.

DETAILED DESCRIPTION OF THE DRAWINGS AND OF THE PREFERRED EMBODIMENTS

General Biochip Structure

The present invention is directed in part to a micro fabricated boichip 20 illustrated schematically in FIG. 1. A silicon wafer substrate or body 22 having a size on the order of a postage stamp is formed with a plurality of receptacles or grooves 24 and 26 which receive ends of respective microbore tubes 28 and 30 made, for instance, of polytetrafluoroethylene. Receptacles 24 and 26 communicate with opposite ends of a meandering microscale channel or groove 32 formed at intervals with cavities or wells 34. Cavities 34 are provided with platinum electrodes 36 which may be coated, as described hereinafter, with molecular probes for selectively capturing target molecules such as antigens on the surfaces of a target bacterium such as *Listeria monocytogenes*. Electrodes 36 are connected to respective bonding pads or electrical terminals 38 via conductors or traces 40.

A glass cover 42 is positioned over receptacles 24 and 26, the ends of tubes 28 and 30, channel 32 and cavities 34 and is sealed to substrate 22. Biochip 20 is thus a self-contained biosensor unit with integrated fluidic paths represented by channel 32 and cavities 34 and electrodes 36 useful in performing micro-scale electronic measurements of biological solutions. The electrodes 36 are spaced from each other by 1 to 100 microns and, more preferably, by 2 to 50 microns.

Figure 2:
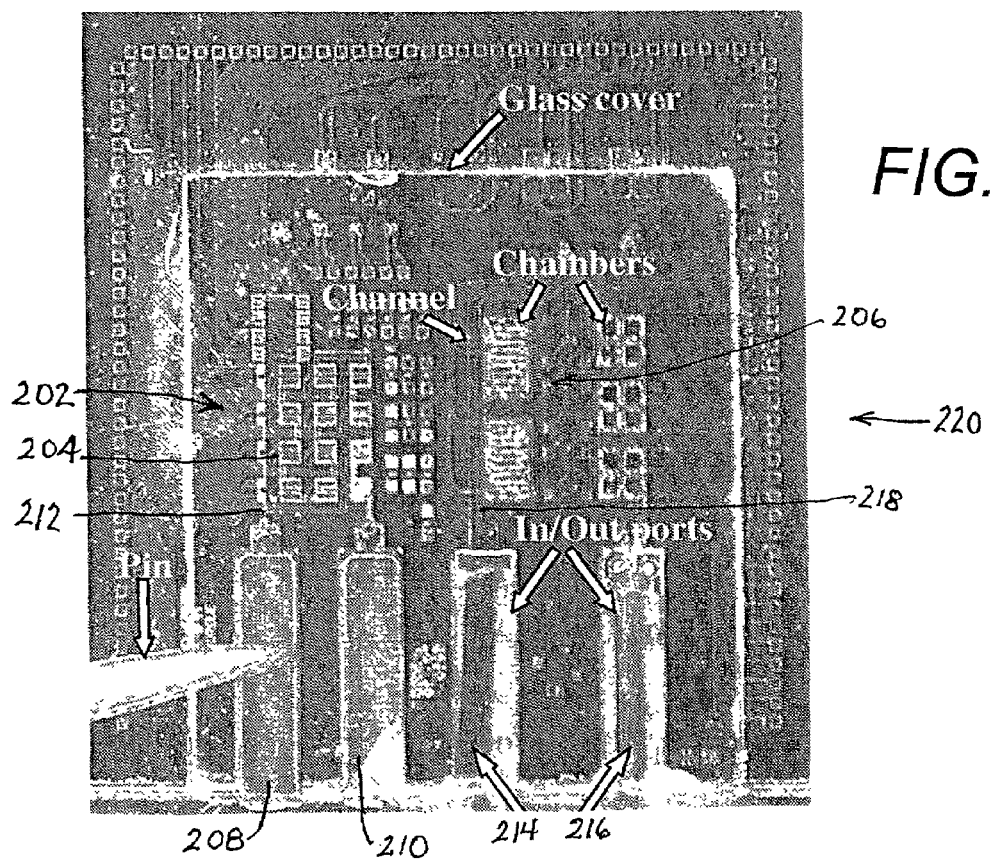
FIG. 2 is a photograph showing, in top plan view, an integrated microscale biosensor in accordance with the present invention.

FIG. 2 is a photograph of a microfluidic boichip 220 as actually manufactured. Biochip 220 includes a first area 202 having electrode-containing cavities 204 of 80 by 80 microns and a second area of electrode-containing cavities 206 of 850 by 530 microns, with a common depth of 10 microns. Cavities 204 are connected to one another and to a pair of tube receptacles or grooves 208 and 210 by a channel or series of channel segments 212, while cavities 206 communicate with each other and with a respective pair of microbore-tube receptacles or in/out ports 214 and 216 via a channel or series of channel segments 218. Cavities 204 contain simple electrodes 36 as shown schematically in FIG. 1, whereas cavities 206 contain electrodes (not designated) having several interdigitated segments.

Figure 3:
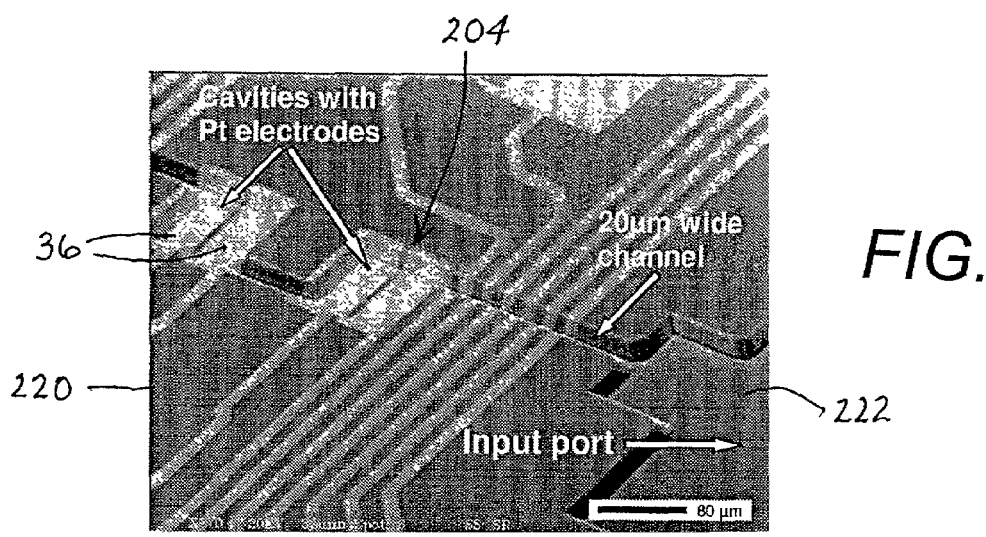
FIG. 3 is a photomicrograph, on a larger scale, of a portion of the biosensor of FIG. 2.
Figure 4:
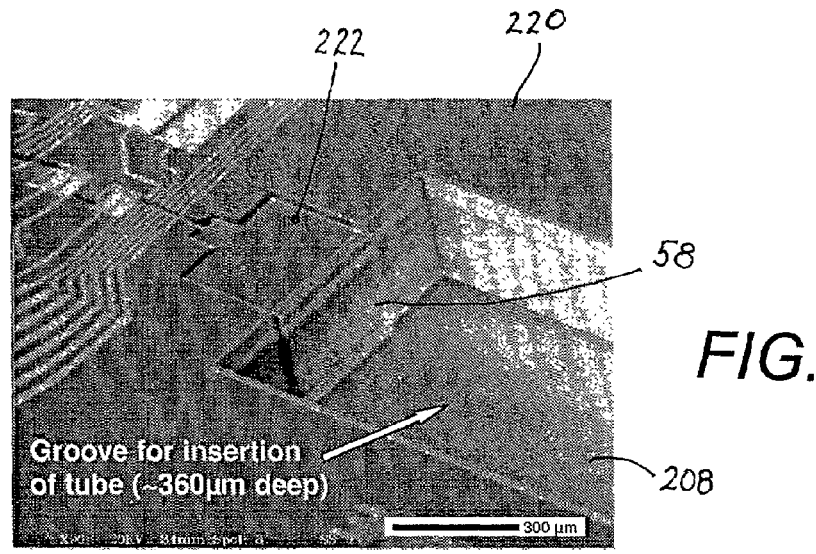
FIG. 4 is a photomicrograph, on an even larger scale, of another portion of the biosensor of FIG. 2.

FIGS. 3 and 4 are scanning electron micrographs, on different scales, of a portion of boichip 220. An inlet port or expanded inlet section 222 of channel 212 is disposed between a respective receptacle or groove 208 or 210.

Figure 5A:
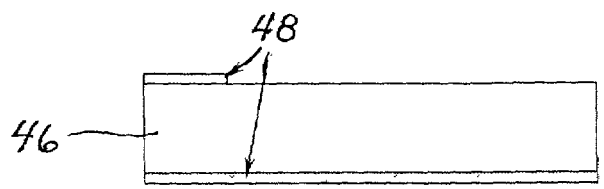
FIGS. 5A through 5F are schematic cross-sectional views, on an enlarged scale, showing successive steps in a process for fabricating a biosensor in accordance with the present invention.
Figure 5B:
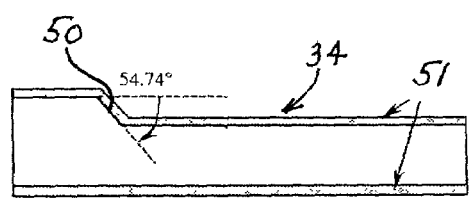
Figure 5C:
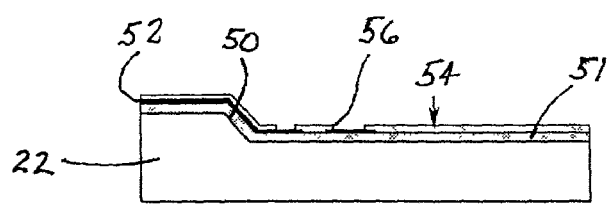

In general, cavities 204 and 204 and channels 212 and 218 were formed by anisotropic KOH-based etching. The process etches the (100) crystal planes about 400 times faster than the (111) planes, creating cavities with walls at an angle of 54.74 degrees, as discussed in greater detail hereinafter with reference to FIG. 5B. RF sputtering of chrome and platinum deposited the electrodes.

Biochip 220 (or generically boichip 20) as disclosed herein has been used to detect and measure a change in conductance in nanoliter volumes of bacterial suspensions and to indicate the viability of the bacteria. Fluid flow through the chip was demonstrated using 2 μm fluorescently labeled beads imaged through a fluorescence microscope. Electrical impedance measurements demonstrate that the device can be used to distinguish between different concentrations of the bacterium *Listeria innocua*, a non-pathogenic strain of *Listeria*, by the change in conductance of the suspension produced by bacterial metabolism. These concentrations correspond to very few bacterial cells in the very small volumes (nanoliters) of the measurement chambers of the biochip.

Manufacturing Process

The manufacture of biochips as disclosed herein will now be described with reference to generic boichip 20. The manufacturing process consists solely of top-side processing to form tube receptacles 24 and 26, channel 32, and cavities or wells 34, on silicon wafer substrate 22. A silicon wafer is used to facilitate a future integration of other electronic detectors or active electronic circuitry in later versions of the chip. The entire fabrication process is depicted in FIGS. 5A through 5F. Silicon wafer blanks 46 (FIG. 5A) with a thickness of 450 μm and (100) orientation are oxidized so as to be provided with 0.45 μm thick $SiO_2$ layers 48, and a series of rectangular cavities 34, connected by channel 32, are etched into the oxide. Potassium Hydroxide (KOH) is used to etch the silicon surface to a depth of about 12 μm using the thermally grown $SiO_2$ as a hard mask. This depth is still within the depth of focus of the mask aligner used, thus guaranteeing a good definition of patterns at the bottom of the etched areas. Since the surface of the wafer is a (100) plane, the etched channels 32 and cavities 34 have tapered walls 50 (FIG. 5B) forming an angle of 54.74° with respect to the oxide surface of the wafer blank 46. Such an angle permits the deposition of metal over the walls 50, allowing for metal traces 40 (FIG. 1) to run into and across the channels 32 without breaks. After the KOH etching, the $SiO_2$ hard mask is completely removed and the wafer is oxidized at 1050° C. for 60 minutes in wet-$O_2$ to form a 0.45 μm thick layer 51 of $SiO_2$ (FIG. 2B). Electrodes 36 at the bottoms of the cavities 34, as well as metal conductors or traces 40 connecting them to the bonding pads 38 on the periphery of the wafer substrate 22, are defined over the oxide layer 48 by lift-off, using a 5 μm thick photoresist layer (AZ4620 from Clariant Corp., New Jersey, U.S.A.). The photoresist layer (not shown) needs to be thick enough to keep it from cracking at the upper edges of the channel walls 50 due to the tension that builds up during baking. A metallization 52 is formed by RF-sputtering of an 800□-thick layer of platinum over a 600□-thick film of chromium, the latter serving as an adhesion layer. The sheet resistance of the metallization 52 is approximately 30 Ω-cm (2.1 Ω/square for the given thickness). After the metal 52 is deposited and patterned, a 0.6 μm thick $SiO_2$ film 54 is deposited by Plasma-Enhanced Chemical Vapor Deposition (PECVD) to insulate the electrodes 36 and traces 40. This film 54 is subsequently wet-etched to open windows 56 (FIG. 5C) and thereby define electrodes 36 and bonding pads 38 (FIG. 1) along a periphery (not designated) of wafer substrate 22. These windows 56 leave only the upper, platinum surface exposed, which is fairly resistant to chemical attack, while keeping the chromium covered so that it does not interact with, or is not affected by any of the solutions that may flow through the channel 32 and cavities 34. (FIGS. 3 and 4 show electron micrographs of a section of boichip 220, where electrodes 36 are defined at the bottom of cavities 204, and metal lines 54 cross the channels 212.)

Figure 5D:
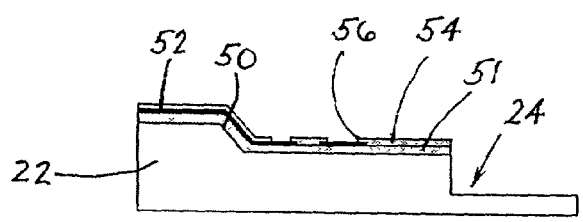

Only after the formation of channel 32 and cavities 34 is the wafer substrate 22 etched to create tube receptacles or grooves 24 and 26 (FIG. 5D). Thereafter, channel 32 and cavities 34 are hermetically sealed to the surface of wafer substrate 22 by bonding cover 42 (FIGS. 1 and 5E), a rectangular piece of glass, 0.17 to 0.25 mm thick (No. 2 Dow Corning microscopy glass cover). Anodic bonding of glass cover 42 may also be possible.

Figure 5E:
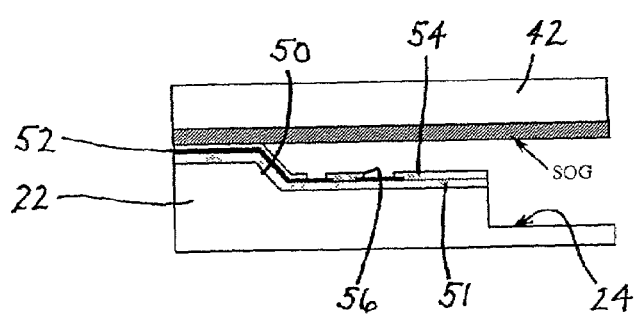

A satisfactory bond is achieved by using a low-melting-temperature Spin-On-Glass (SOG) as adhesive (FIG. 5E). This SOG is methylsilsesquioxane polymer (Methylsilsesquioxane 400F from Filmtronics Inc., Pennsylvania, U.S.A.) that flows at temperatures between 150° C. and 210° C. The flowing SOG fills the grooves in between the platinum traces 40 and any other surface irregularities, providing a perfectly hermetic seal, while the low flow temperature minimizes thermally induced stresses and damage to temperature-sensitive materials on the die or wafer substrate 22. The glass cover 42 is first cut to the desired size in a diamond saw, thoroughly rinsed in DI water, dried, and cleaned in $Ar/O_2$ plasma for 20 minutes. After cleaning, the SOG is spun on the glass at 5000 rpm for 40 s and dried in a convection oven at 90° C. for 2 minutes. This process results in a SOG film approximately 3000 Å thick according to the data-sheet provided by the manufacturer (Spin-on-Glass, 1998). The glass is then manually aligned onto the substrate 22 (SOG side down) and clamped in place. Subsequently, the clamped assembly is heated on a hot plate to 100° C. for 5 minutes, followed by 180° C. for 5 minutes, and 200° C. for at least 1 hour to cure the SOG film. Although the manufacturer indicates that the SOG must be cured at 400° C. for 30 minutes, extensive cracking of the SOG film was observed if the bonded assembly was exposed to temperatures above 300° C. Most likely, the cause of this cracking is the large mismatch between the thermal expansion coefficients of silicon substrate 22, glass cover 42, and the SOG. For this reason, to minimize the stress in the SOG film the curing temperature is kept at 200° C., which seems to be sufficient for a reliable bond. The curing time could be substantially increased to compensate for the lower temperature, but even a one hour cure produces a bond capable of withstanding the maximum pressures that have been applied to drive fluids through micro-channel 32. A single pressurization test of one fully functional boichip 20, with no flow, indicated a failure pressure of approximately 700 kPa. At this pressure the glass started to unbind from the chip and leaks appeared in the region around the input/output receptacles or grooves 24 and 26.

One of the challenges that exists in the development of microfluidic biochips is creating reliable fluidic interfaces to the macro-world. For boichip 20, connections for injecting samples into the device are created by etching receptacles or grooves 24 and 26 deeply running up to the edge of substrate 22, so that microbore tubes 28 and 30 can be inserted horizontally or laterally as depicted in FIG. 1. This configuration has several advantages over the standard top connection through the sealing cover. The length of tube receptacles 24 and 26 can be adjusted to provide a large bonding surface which improves the robustness and reliability of the connection to the microbore tubes 28 and 30; in this case receptacles 24 and 26 were made 2 mm long and 700 µm wide. Locating tubes 28 and 30 horizontally results in a planar structure that is easier to package and handle. And there is no need for fine alignment between channel 32 (or cavities 34) on the silicon substrate 22 and sealing cover 42, which would be necessary if the input/output ports were on cover 42. The receptacles 24 and 26 are created by a Deep Reactive Ion Etch (DRIE) system (Plasma Therm SLR770 system using the Bosch Etch process), to a depth of approximately 390 µm, with a 10 µm photoresist layer as mask (FIG. 5D). The etch-rate is about 1.6 µm/min with a selectivity to photoresist of approximately 75:1. (A protrusion 58 at the edge between inlet section 222 of channel 212 and receptacle or groove 208 (FIG. 4) appears because the photoresist hardmask flows during the bake step prior to the DRIE.)

Figure 5F:
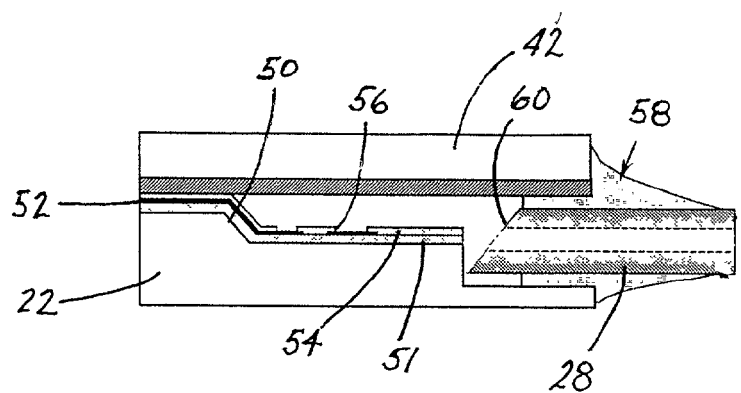

Tubes 28 and 30 are bonded into the trenches after the glass cover is attached to the device. Before bonding, the tips of the tubes 28 and 30 are treated with FluoroEtch (Acton Technologies Inc., Pennsylvania, U.S.A.) to improve their bondability (by forming a carbonaceous layer on the surface). Tubes 28 and 30 are cut at an angle at 60 to keep the respective bores from being blocked by the inner walls (not separately labeled) of receptacles 24 and 26. Tubes 28 and 30 are inserted into receptacles 24 and 26 and the remaining voids in the receptacles are filled with biomedical grade epoxy adhesive 58 (Durabond M-121HP from Loctite Corp., Connecticut, U.S.A.), which penetrates into the receptacles 24 and 26 by capillarity (FIG. 5F). Even very rough handling of the tubes 28 and 30 does not compromise the integrity of the bond.

Impedance of Bacterial Suspensions

There have been publications describing the detection of pathogenic bacteria in food by monitoring the conductance or the impedance of a specially formulated culture medium innoculated with extracts from food samples. This is possible because bacterial metabolism changes the electrolyte concentration in the suspension medium, significantly altering the electrical characteristics of the medium. Most of these conductivity measurements are performed with DC signals, yielding no information about interfacial phenomena at the solution-electrode interfaces. But Felice et al. ("Impedance Microbiology: Quantification of Bactrial Content in Milk by Means of Capacitance Growth Curves," *Journal of Microbiological Methods*, vol. 35, pp. 37-42, 1999) claim that measuring some of the interfacial parameters using an AC excitation (at a single frequency, or preferably at multiple frequencies) makes the technique more sensitive.

Figure 6:
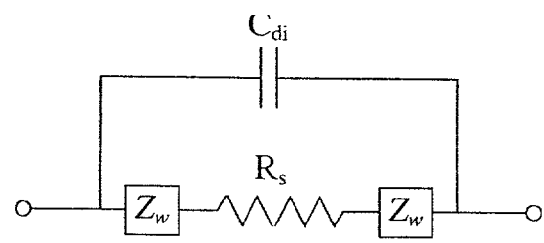
FIG. 6 is a circuit diagram modeling electrical activity in a biosensor as illustrated in FIG. 1 or FIGS. 2-4.

A fairly simple circuit model of a pair of electrodes immersed in an electrolytic solution is shown in FIG. 6 (see Jacobs et al., "Impedimetric Detection of Nucleic Acid Hybrids," *Proceedings of the Second International Conference on Microreaction Technology*, New Orleans, La., pp. 223-229, 1998), where $C_{d1}$ is the dielectric capacitance (incorporating contributions from all the materials surrounding the electrodes 36, including the solution), $R_S$ is the bulk solution resistance (charge transport across the bulk), and $Z_W$ is the interfacial impedance (the so-called Warburg impedance), which accounts for the changes in the electrolyte concentration gradient at the interface. The simplest model of the interfacial response to AC signals, yields the following expression for:

$$Z_\omega = \frac{\sigma(1-j)}{\omega^{1/2}}$$

where $j=(-1)^{1/2}$, $\omega$ is the angular frequency of the electrical signal, and $\sigma$ is a parameter that depends on the diffusive properties of the electrolytes, and the area and characteristics of the electrodes. From this expression we can see that the phase difference between the applied voltage and the resulting current will be 45° at all frequencies. However, actual systems show that the phase difference can be anywhere between 0° and 90°, while still remaining constant over frequency. Thus, a better model for the interfacial impedance is (see Jacobs et al., "Impedimetric Detection of Nucleic Acid Hybrids," *Proceedings of the Second International Conference on Microreaction Technology*, New Orleans, La., pp. 223-229, 1998):

$$Z_\omega = \frac{1}{(j\omega)^n B}$$

where n and B are parameters that depend on the properties of the electrolytes and of the electrodes. This equation assumes that the phase between voltage and current is constant at $n\pi/2$ rad. It is to be noted that the impedance Z is a measured parameter, whereas n and B are extracted parameters.

Preliminary experiments to study the effects of bacterial metabolism on the electrical properties of the suspension medium were carried out using boichip 220 (FIGS. 2-4). The main purpose of these experiments was to determine whether impedance measurements in the microscale could provide information about the metabolic activity of a small number of bacteria. Metabolic activity could then be used as an indicator of bacterial viability. Impedance measurements were done in a chamber or cavity 206 that was 530 μm wide by 850 μm long by 12 μm deep, for a total volume of 5.27 nl (taking into account that the walls of the well have a 54.74° angle). This chamber 206 had two interdigitated platinum electrodes (not shown) with five fingers each. The exposed area of each finger was 450 μm by 50 μm, and the distance between finger centers was 80 μm. A HP4284A LCR meter (Hewlett Packard Corp., now Agilent Technologies, Palo Alto, Calif.) measured the impedance of the interdigitated electrodes at 52 frequencies, logarithmically spaced between 100 Hz and 1 MHz, with a 50 mV (amplitude) voltage excitation. The impedance of the wiring and probes was automatically substracted from the measurements, so that only the impedance of the elements in the biochip 220 was recorded.

*Listeria innocua* was cultured in Brain Heart Infusion (BHI) broth (Difco Laboratories, Detroit, Mich.) for 16 hours at 37° C., then washed four times by centrifugation and re-suspension in a low conductivity Tris-Glycine (Tris-Gly) buffer to eliminate all the electrolytes present in the culture broth. The Tris-Gly buffer contained 3.6 mM Tris, approximately 4.7 mM Glycine, plus 0.05% (vol/vol) Tween-20 (a detergent). This detergent is necessary to prevent sticking of the cells to each other and to biochip 220, which would clog the microscopic channels 212, 218 in the biochip. The nominal pH and conductivity of the buffer were 7.4 and 33.5 μS/cm, respectively. The Glycine concentration was modified around the nominal value to adjust the pH close to 7.4. Previous (unpublished) macro-scale experiments using live and heat-killed *L. innocua* had clearly indicated that the bacteria remain alive in the Tris-Gly buffer and that their metabolism does indeed change the buffer conductance. After washing, the bacteria were re-suspended at concentrations of about $10^5$, about $10^7$, about $10^8$, and about $10^9$, cells/ml in the Tris-Gly buffer. These concentrations resulted in approximately 0.53, 53, 530, and 5300 bacterial cells (in average) in the 5.27 nl chamber or cavity 206 (FIGS. 2 and 6), respectively. Afterwards, dextrose was added to each suspension at a concentration of 2.2 mg/ml and the suspensions were incubated at 37° C. for 2 hours to promote bacterial growth, along with a sample of buffer with dextrose, without bacteria, as control. Following incubation, the samples were refrigerated at 2° C. until the measurements were performed. All samples were injected into boichip 220 using pressurized nitrogen, and were allowed to flow through the chip for 15 minutes, before measuring, to properly flush the whole fluidic path.

Figure 7:
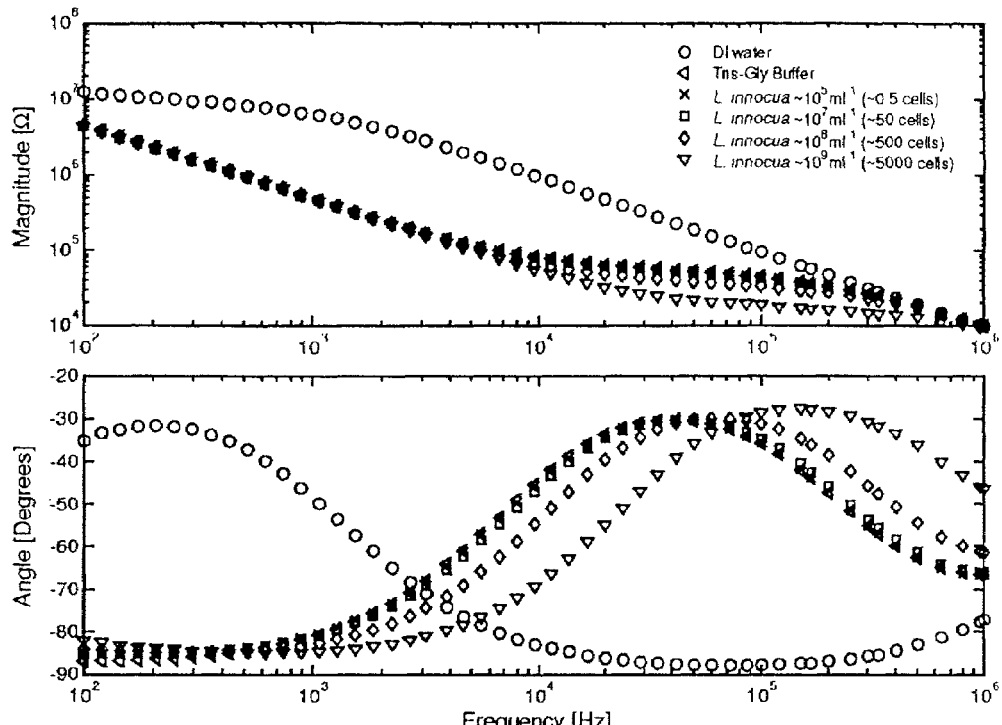
FIG. 7 is a pair of graphs showing measured complex impedance (magnitude and angle) of different microorganism-containing samples injected into a boichip in accordance with the present invention. The numbers of cells in the legend correspond to the numbers present in a detection chamber of the boichip where the measurement was performed.
Figure 8:
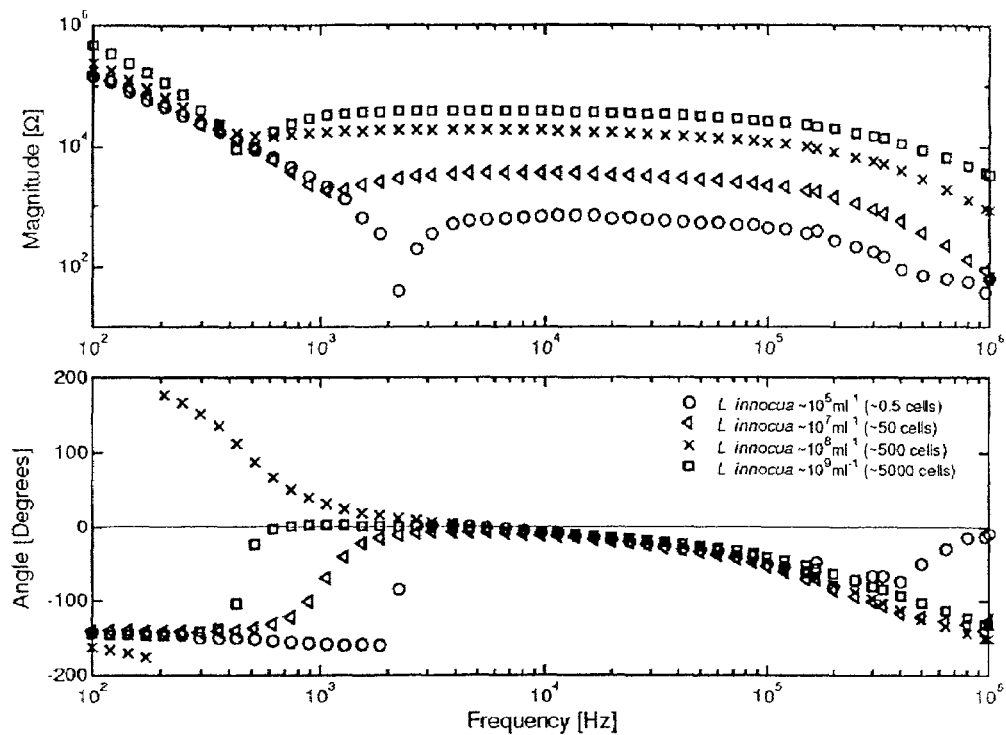
FIG. 8 is a pair of graphs showing differences between the complex impedance of a Tris-Gly buffer and each one of the different samples injected into the biochip. Again, the numbers of cells in the legend correspond to the numbers present in a detection chamber of the biochip where the measurement was performed (vol.=5.27 nl).
Figure 9:
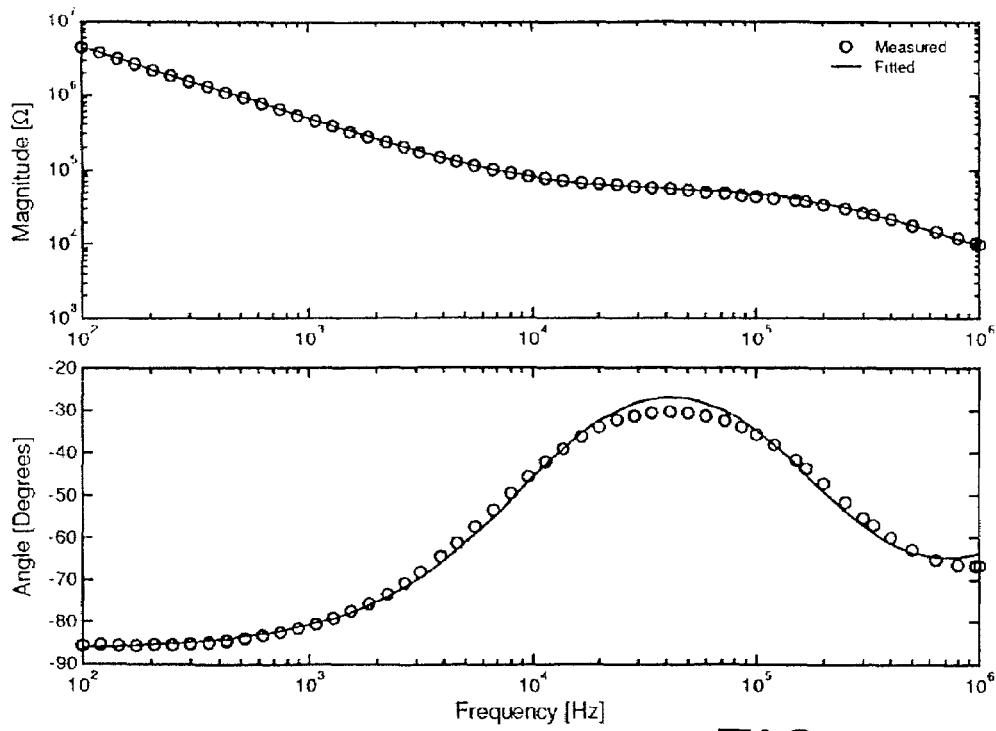
FIG. 9 is a pair of graphs of complex impedance (magnitude and angle vs. frequency), showing a fit between the circuit model of FIG. 6 and the measured complex impedance of the microorganism-containing samples at a concentration of approximately $10^5$ cells/ml.

FIG. 7 shows the complex impedance (magnitude and angle) as a function of frequency for six different samples injected into boichip 220: De-ionized (DI) water with a conductivity of 0.06 μS/cm, Tris-Gly buffer with 2.2 mg/ml dextrose, and the four *L. innocua* suspensions mentioned above. FIG. 8 shows the difference between the measured complex impedance of Tris-Gly buffer and the impedance of each one of the *L. innocua* suspensions ($\Delta Z = Z_{buffer} - Z_{bacteria}$). For frequencies between 2 kHz and 20 kHz, most of the difference in impedance from buffer to each one of the suspensions is due to changes in the resistive components, as evidenced by a phase close to 0° for $\Delta Z$ in this frequency range. The circuit model shown in FIG. 6 was fitted to the measured curves, with $Z_\omega$ given by the equation:

$$Z_\omega = \frac{1}{(j\omega)^n B}$$

described above, and an additional series resistor $R_{tr}$ that accounts for the resistance of the metal traces on the boichip 220 (FIGS. 2-4), connecting the bonding pads 38 (FIG. 1) to the electrodes 36 in the chamber 206 (FIG. 2). Values of $R_{tr}$=2889 Ω and $C_{di}$=17.98 pF were extracted from fitting to the Tris-Gly buffer data and held fixed when fitting the model to all other samples. FIG. 9 shows an example of how well the chosen model fits the measured impedances. The values of $R_s$, n, and B obtained from the fits to all the samples are contained in Table 1.

TABLE 1

Parameters resulting from fitting the circuit model of FIG. 6 to the impedance data shown in FIG. 7.

| Sample | Number of Cells In 5.27 nl | Bulk Solution Resistance $R_s$ [kΩ] | n | B [×10⁻¹²] |
|---|---|---|---|---|
| DI water | 0 | 242.0 | 0.149 | 5.83 × 10⁴ |
| Tris-Glys Buffer | 0 | 56.58 | 0.968 | 800.6 |
| about 10⁵ cells/ml | 0.527 | 55.26 | 0.961 | 857.6 |
| about 10⁷ cells/ml | 52.7 | 51.98 | 0.960 | 869.7 |
| about 10⁸ cells/ml | 52.7 | 35.54 | 0.952 | 915.5 |
| about 10⁹ cells/ml | 5270 | 15.01 | 0.945 | 1003.1 |

Figure 10:
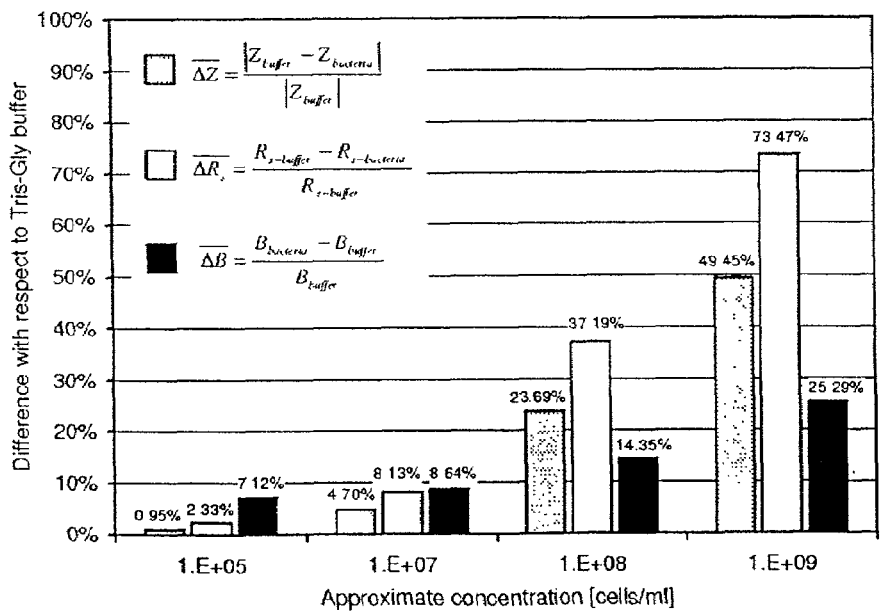
FIG. 10 is a bar graph showing normalized differences of three measurement parameters for each microorganism-containing sample injected into the boichip as described herein.

Having n close to 1.0 for all samples, with the exception of DI water, indicates that the interface is mostly capacitive, with a small parallel resistive component. FIG. 10 compares the following normalized differences for the various cell concentrations:

$$\Delta Z = \frac{|Z_{buffer} - Z_{bacteria}|}{|Z_{buffer}|}, \text{ at } f = 11.43 \text{ kHZ}$$

$$\overline{\Delta R_s} = \frac{R_{s-buffer} - R_{s-bacteria}}{R_{s-buffer}}$$

$$\overline{\Delta B} = \frac{B_{bacteria} - B_{buffer}}{B_{bacteria}}$$

At the lowest concentration, the difference in B is larger than that in Z and $R_s$, while above $10^7$, cells/ml $R_s$ shows the largest differences with respect to buffer. Detection can rely on both $\overline{\Delta R_s}$ and $\overline{\Delta B}$ to increase the sensitivity at the lowest concentrations. These results indicate that if the small number of *Listeria* cells present in a food or soil sample can be captured and retained in a chamber in the biochip, their viability could be assessed by measuring the change in impedance of the electrodes 36 in the detection chamber or cavity 34, 204, 206. Fewer than 10 cells in a 5.27 nl volume could in principle produce a change of ~7% in the parameter B, provided that any ionic contamination coming from the sample can be completely removed and that the chamber is filled with a low conductivity buffer (with appropriate nutrients to promote growth), as described in further detail below.

Figure 11:
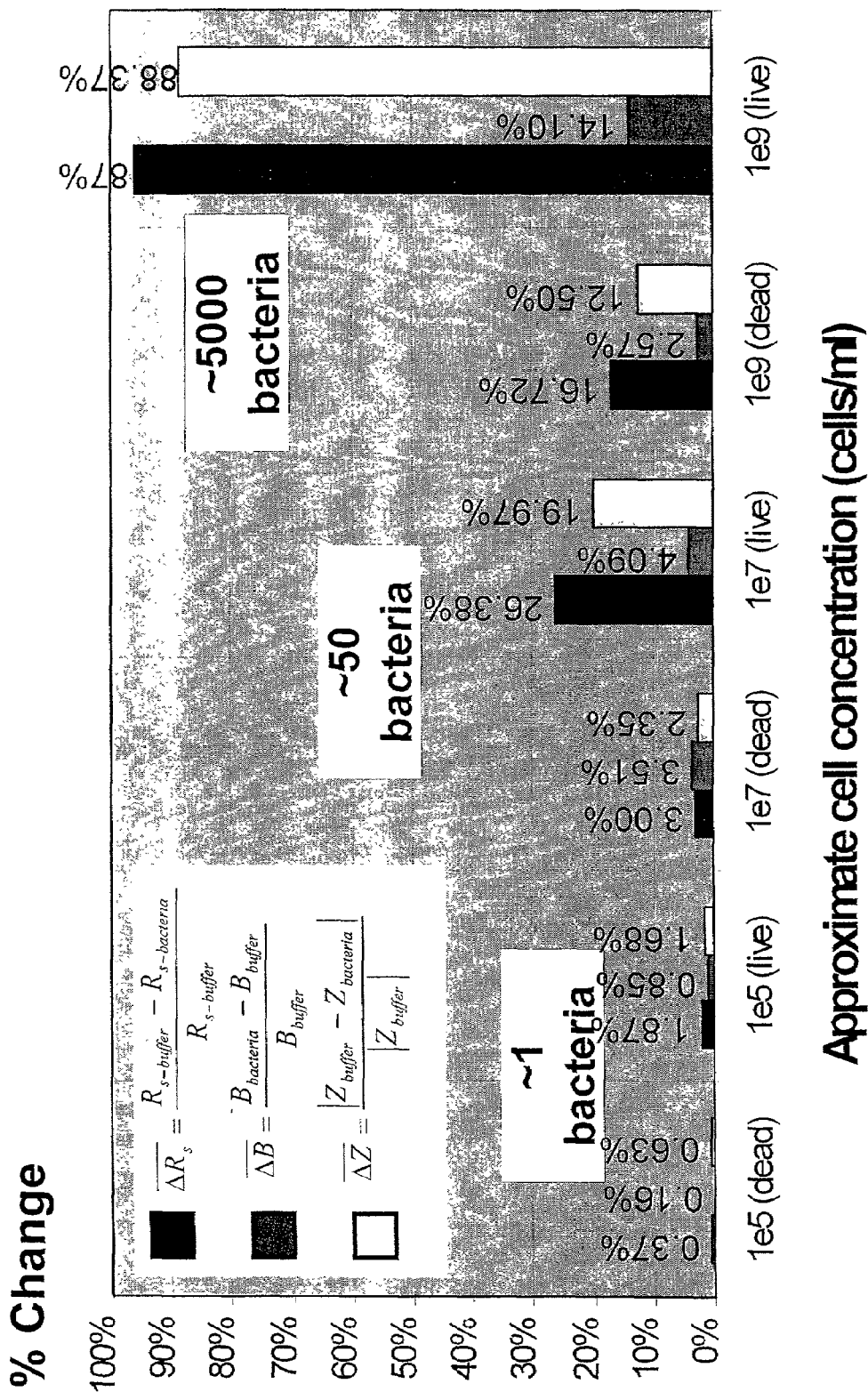
FIG. 11 is a bar graph similar to FIG. 10, showing normalized differences of three measurement parameters for each of several live-microorganism-containing samples and each of several dead-microorganism-containing samples injected into a boichip as described herein, demonstrating an ability to distinguish between live and dead microorganisms.

FIG. 11 is a bar graph similar to FIG. 10 and shows normalized differences of the above three measurement parameters for four concentrations of live *Listeria innocua* and four like concentrations of dead *Listeria innouca* cells.

These results indicate that the viability of a captured sample of microorganisms could be assessed by measuring the change in impedance of the electrodes 36 in the detection chamber or cavity 34, 204, 206.

The quantity $\Delta Z$ is sufficient in many cases to enable detection of a target microbiological species or substance. In other cases, $\Delta R_s$ is a more sensitive value.

It is to be noted that impedance is significantly different between buffer alone, and buffer containing microorganisms. Detection of 10 to 100 microorganisms is feasible. Where the electrode spacing is small (e.g., about one to three microns), detection results not only directly from the presence of the microorganisms in effective contact with the electrodes, but also indirectly from a change in electrolyte concentration in the liquid matrix close about the microorganisms, owing to the metabolic activity of the organisms. Where the electrode spacing is 5 microns or larger, bulk impedance is measured to study the effect of bacterial metabolism in the environment of the chambers, as discussed in detail below. In both approaches, the measurement of impedance reflects the generation of metabolites of cells and therefore gives a measure of whether the cells are living or dead.

Bioseparations Process

A method utilizing boichip 20 or 220 to detect the presence of a target microbiological entity such as a pathogenic strain of bacteria preferably includes a purification or bioseparations process performed immediately prior to, and optionally upon, injection into boichip 20 or 220. This bioseparations process serves to remove, from the fluid sample tested in the detection chamber or cavity 34, 204, 206 of the boichip 20, 220, molecular and cellular detritus which would impede the accurate detection of the target species. The removal of such molecular and cellular detritus increases the signal-to-noise ratio and thus improves the accuracy and reliability of the measurement process.

Figure 12:
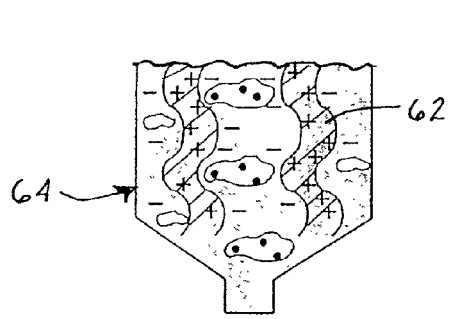
FIG. 12 is a schematic cross-sectional view of a pipette tip with structure for preparing a biological sample for testing with a biosensor in accordance with the present invention.
Figure 13:
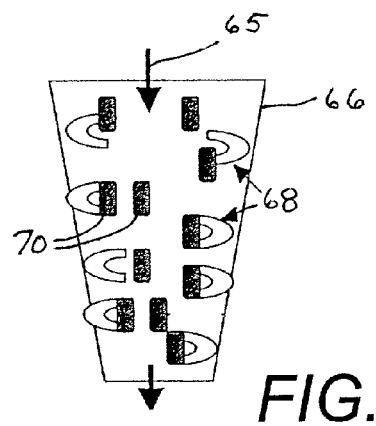
FIG. 13 is a schematic cross-sectional view of an ancillary pipette tip with respective structure for preparing a biological sample for testing with a biosensor in accordance with the present invention.

In general, a bioseparations process as contemplated herein may utilize bioactive fibers and/or surfaces 62 exemplarily of cotton (cellulose) and packaged into a micropipette tip 64, as depicted schematically in FIG. 12. Pipette tip 64 is inserted into a specimen of bodily fluids, foodstuffs, soil, etc., and operated (e.g., via a suction source such as a syringe-type plunger) to aspirate a raw fluid from the specimen. Bioactive fibers and/or surfaces 62 function to remove colloidal particles and extraneous proteins and to that end are derivatized with cation and/or anion ion exchange groups (represented in FIG. 12 by "+" and "−" signs) using established technology (Ladisch et al., 1997, 1998). Fibers and surfaces 62 are packed loosely enough to allow a raw fluid sample to be aspirated from a specimen. The ion exchanger and appropriate conditions are selected so that the targets cells do not bind (see Ladisch, 1997) and can be injected, as indicated by an arrow 65, into a second pipette tip 66 (FIG. 13) containing polyclonal antibodies 68 for the concentration of both pathogenic and nonpathogenic bacteria 70, for instance, different species of Listeria. Polyclonal antibodies 68 are either immobilized to a fiber 62 or fixed to the inner surfaces of pipette tip 66. The sample is then rinsed with a buffer solution, e.g., a phosphate buffer solution, to remove extraneous fluid. This sample is then pH modified and injected into microbore tube 28 (FIG. 1) for measurement. These preparation steps can be performed rapidly, within several minutes.

Figure 14A:
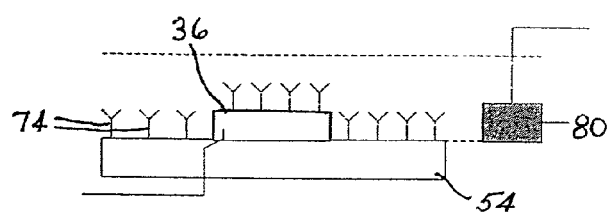
FIGS. 14A through 14C are diagrams showing successive stages in manufacturing and testing processes for automated detection of microorganisms with a biosensor or boichip as illustrated in FIG. 1 or FIGS. 2-4.
Figure 14B:
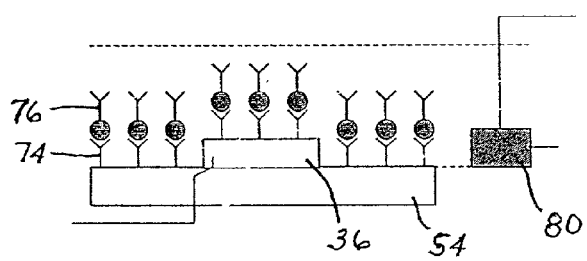
Figure 14C:
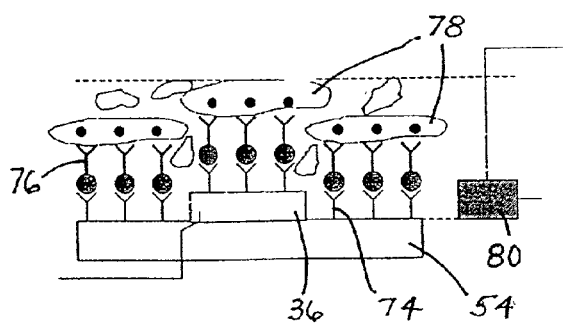

Alternatively or additionally, the affinity binding of a target bacterium such as Listeria monocytogenes to an antibody may be effectuated inside the boichip 20, 220 and more particularly inside the detection chambers or cavities 34, 204, 206. The antibodies are attached to the electrodes 36 (FIG. 1) via avidin-biotin coupling. The antibodies are biotinylated, i.e., chemically bonded to the biotin and the biotin is in turn adhered to avidin adsorbed onto the surfaces of electrodes 36. FIG. 14A depicts avidin molecules 74 adsorbed onto an electrode 36, as well as onto surrounding silicon oxide 54 (see FIGS. 5A-5F). FIG. 14B shows biotinylated antibodies 76 attached to the adsorbed avidin molecules 74. In FIG. 14C, target bacteria cells 78 are depicted coupled to the biotinylated antibodies 76 and hence to electrode 36 and oxide 54. A difference in electrical measurements between electrode 36 and a reference electrode 80 indicates the presence of target cells 78 in the detection chamber or cavity.

The adsorption of avidin molecules 74 onto electrodes 36 of boichip 20 or 220 may be implemented as follows. Avidin is dissolved in 10 mM HEPES buffer containing 0.1 M NaCl, to obtain a concentration of the avidin of 5 mg/mL. The buffer has a pH of 8.5 and contains 0.08% sodium azide to prevent microbial growth. The avidin solution is then diluted with PBS (phosphate buffer saline) at a ratio of 0.2 mL to 0.8 mL to obtain a final concentration of 1 mg/mL. The chip 20, 220 is then immersed in this solution, e.g., 1 mL thereof, overnight at room temperature. The antibodies are derivatized with biotin using conventional techniques, while the biotinylated antibodies are applied to the biosensor chip using the same methodology as used in adsorbing the avidin. Finally, all chips are rinsed in PBS for 5 minutes at room temperature.

In the case of Listeria monocytogenes, highly selective antibodies that will bind the 66-kDA protein found on the surface of pathogenic Listeria monocytogenes cells are used as a binding agent or part of a binding agent. Monoclonal antibody producing clones of C11E9 and EM-7G1 (producing antibodies specific for Listeria monocytogenes) are cultured in growth media in a growth chamber. Antibodies are harvested from culture supernatants by salt (ammonium sulfate) precipitation. After an initial concentration step, carried out by known techniques, high quality antibodies are obtained by further purification through size exclusion chromatography followed by protein-A affinity chromatography in an FPLC system.

Testing of Bioseparations Media

Concentration of target pathogenic cells and removal of extraneous microbiological detritus from fluid samples are important for maximizing the signal to noise ratio on boichip 20, 220. Research on bioseparations steps has demonstrated that either an anion or cation exchange resin can remove 50 to 80% of the protein from hot-dog juice, i.e., the liquid material that is extracted from a hot dog which is to be tested for Listeria monocytogenes. While protein removal would typically be expected as indicated by initial runs made with pure protein solutions in which bovine serum albumin (BSA) was dissolved in buffer, testing of the same anion exchange materials with hot-dog serum showed only a small extent of protein removal. This led to a more detailed study in which 15 soluble proteins in the serum were identified, and their change in concentration over a 100-min period quantified using liquid chromatography. Testing with a number of different adsorbents (Table 2) consisting of strong and weak cation and anion exchange resins, silica, hydroxyapetite, hydrophobic interaction material, and polymeric adsorbents, showed only two of these gave a large decrease in all of the protein peaks. A ten to twenty minute contact time is sufficient to achieve protein removal using either a strong cation or strong anion exchanger. Fluorescence microscopy shows that *Listeria innocua* cells do not adsorb onto the resin particle. An antibody attached to the resin particle is needed if a solid adsorbent is to be used to capture cells. Conversely, the inability of many of these resins to adsorb proteins from the hot-dog juice also makes them candidates for selectively adsorbing cells (but not proteins) if an appropriate antibody for the cell is attached to these materials. Protein removal could also be followed by cell-concentration using membrane microfilters.

TABLE 2

Chromatographic Supports Tested for Protein Removal from Hotdog Juice

| Experiments | Resin ID | Functionality |
|---|---|---|
| 1 | DEAE 650M | Weak anion exchanger |
| 2 | Super-Q-650M | Strong anion exchanger |
| 3 | QAE-550C | Strong anion exchanger |
| 4 | IRA 400 | Strong anion exchanger |
| 5 | DEAE Cellulose | Weak anion exchanger |
| 6 | IR-120+ | Strong cation exchanger |
| 7 | Amberlite XAD-2 | Polyaromatic adsorbent |
| 8 | Butyl-650s | Hydrophobic interation support |
| 9 | Amberlite IRN-150 | Mixed bed ion exchanger |
| 10 | Amberlyst 35 | Strong cation exchanger |
| 11 | Hydroxylapatite | Inorganic adsorbent |
| 12 | Silica $SiO_2$ | Inorganic adsorbent |
| 13 | SP 550 | Strong cation exchanger | remove these other non-protein compounds in addition to the protein present in the hotdog juice extract.

For the screening study, three replicate chromatography runs of the hot-dog juice extract were used to calculate the "total protein peak area" or the 100% point on the plot. A total of 15 peaks were used as a benchmark for this comparison. The areas of these 15 peaks were totaled to give "total peak area." Values for the three replicate runs were then averaged together for the initial total protein peak area. Only a single injection of each time course study sample was made. Areas for each of the 15 components corresponding to the original time "0" sample were added together and compared against time "0." Plots show % total "Protein Peak Area" remaining at each time course point in the study. Results from the four most promising sorbents are shown: IRA 400, A-35, IRA 120+ and IRN-150. Of these four finalists, the top cation exchanger A-35 and the top anion exchanger IRA 400 were chosen for the final study. The screening study designed to measure the time course of adsorption monitored the "total protein" peak area remaining after exposure to the series of sorbents. In the final set of runs each of the 15 benchmark peaks in the hotdog juice extract were followed after a 30 minute exposure to the sorbents. A figure is provided to give a visual representation to the numeric data for the IRA 400 experiment. As shown, the IRA 400 drops the peak maximums from 0.25-0.5 absorbance units to less than 0.10 AU. Results from these three final experiments suggest that the IRA 400 alone is the best choice for cleaning up the hot-dog juice extract. Doubling the amount of IRA 400 from 5 to 10 grams approximately doubles the extent of protein removal.

TABLE 3

Protein Removed by Cation and Anion Exchangers (10 g total wt. in 50 mL Hot-dog Juice. Analysis: Dynamax $C_{18}$ Column 0–100% CAN in 35 min gradient

| Peak # | RT (min) | Blank Hotdog Juice ini. Peak Area | A35 (2 ×) Peak Area | % Reduction | IRA400 (2 ×) Peak Area | % Reduction | A35 + IRA400 Peak Area | % Reduction |
|---|---|---|---|---|---|---|---|---|
| 1 | 4.16 | 207575 | 133322 | 35.77 | 409904 | 80.25 | 104719 | 49.55 |
| 2 | 4.61 | 814650 | 673801 | 17.3 | 368994 | 54.71 | 585553 | 28.12 |
| 3 | 4.87 | 646233 | 376351 | 41.76 | 163097 | 74.76 | 360256 | 44.25 |
| 4 | 5.45 | 359038 | 153059 | 54.76 | 422584 | 88.26 | 142949 | 60.27 |
| 5 | 6.29 | 243742 | 205337 | 15.76 | 781038 | 68.0 | 937024 | 61.56 |
| 6 | 6.73 | 411003 | 212429 | 48.31 | 0 | 100.0 | 222436 | 45.88 |
| 7 | 7.41 | 456497 | 182578 | 60.00 | 0 | 100.0 | 76955 | 83.14 |
| 8 | 9.13 | 403089 | 240411 | 40.36 | 81659 | 79.74 | 37731 | 90.64 |
| 9 | 9.5 | 417685 | 268091 | 35.74 | 118727 | 71.54 | 312408 | 25.11 |
| 10 | 10.40 | 481247 | 392557 | 18.43 | 550753 | 0 | 326840 | 32.08 |
| 11 | 11.40 | 319132 | 0 | 100.0 | 88895 | 72.14 | 27663 | 91.33 |
| 12 | 11.80 | 222569 | 108530 | 51.24 | 28084 | 87.38 | 87965 | 60.48 |
| 13 | 12.5 | 326507 | 188755 | 42.19 | 43263 | 86.75 | 135401 | 58.53 |
| 14 | 13.5 | 105266 | 72316 | 31.3 | 17966 | 82.93 | 64559 | 38.67 |
| 15 | 14.0 | 117063 | 17293 | 85.23 | 17828 | 84.77 | 13650 | 88.34 |
| Total | | 16,586,152 | 10,063,117 | 39.33 | 4,161,338 | 74.91 | 8,476,811 | 48.89 |

Figure 15:
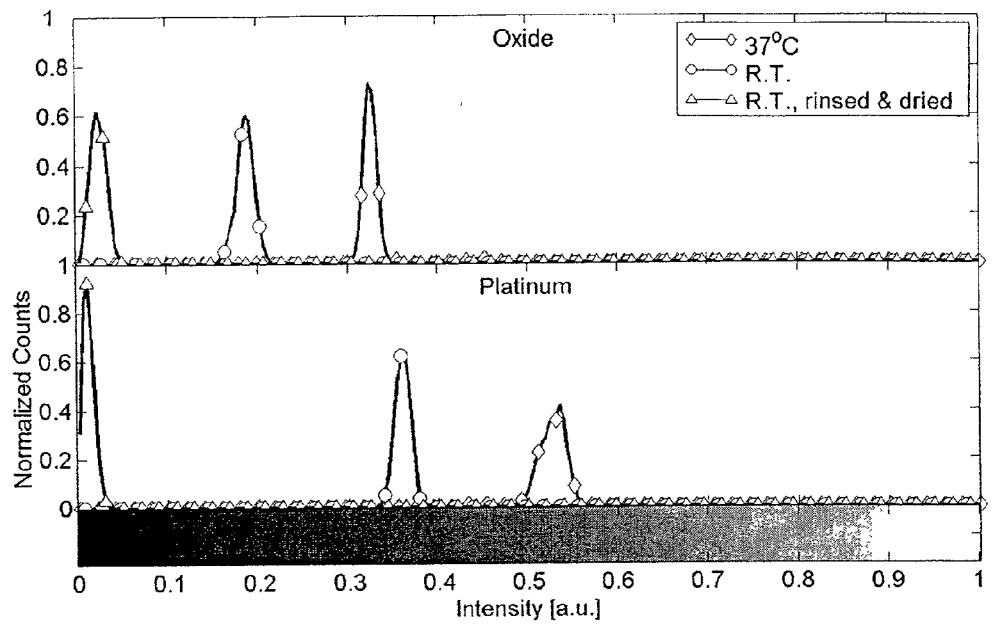
FIG. 15 is a pair of histogram graphs plotting fluorescence emission from surfaces of a biosensor or boichip incubated in 1 mg/mL avidin at room temperature for 18 hours and at 37° C. for 15 hours and then rinsed in DI water followed by drying with compressed air.

HPLC analysis of the supernatant samples removed during the time course studies were used to generate the results shown in this report, Bradford protein assays were also run on the same samples in parallel. Assay results were inconclusive due to interference from non-protein compounds in the samples. UV absorbance was greater at 260 nm than 280 nm for many of the peaks suggesting the presence of DNA fragments and other UV absorbing non-protein compounds in the hot-dog juice extract. Chromatographic sorbents designated as optimal (A-35 and IRA 400) were shown to Testing of Avidin-Biotin Complexing on Biochip Substrate In tests of avidin adsorbed onto electrodes and oxide surfaces of a boichip as described hereinabove, fluorescence microscopy confirmed binding of fluorescein labeled ImmunoPure Avidin (Pierce, Rockford, Ill., Cat.#21221, Lot#AI612511). Avidin is a glycoprotein (MW=68 k Da) in egg white with an isoelectric point of about 10. Since adsorption is carried out below the isoelectric point, the avidin carries a positive charge at the conditions of these experiments. The avidin solution contacted with the chip was prepared from 0.2 mL of 5 mg/ml protein stock solution in 10 mM HEPES, 0.15M NaCl, and 0.08% sodium azide buffer (as supplied by Pierce) diluted with 0.8 mL PBS, pH 7.4, to obtain a protein concentration of 1 mg/mL. The chip was then placed in 0.2 mL of this solution for 15 hours at either room temperature or 37° C. The chips were immersed (rinsed) 3 times in PBS for 5 min each time to remove excess protein. The protein remaining on the chip was then measured using fluorescence microscopy at room temperature. Histograms of fluorescence intensity from the surface of the chip generated using MatLab and image analysis software, show that more protein binds on the platinum than the silicon oxide and that more adsorption occurs at 37° C. than at room temperature (FIG. 15). In the histogram graphs of FIG. 15, peaks on the right side coincided with highest emission. The protein adsorbed at room temperature is removed when the chip is rinsed (dipped) in deionized water for 30 sec and then dried by a blast of dry compressed (120 psig) air for 15 sec. The result confirms that avidin is readily be absorbed onto both the silicon dioxide (e.g., oxide) and platinum surfaces of a chip in a wet state and removed in a dry state.

Figure 16:
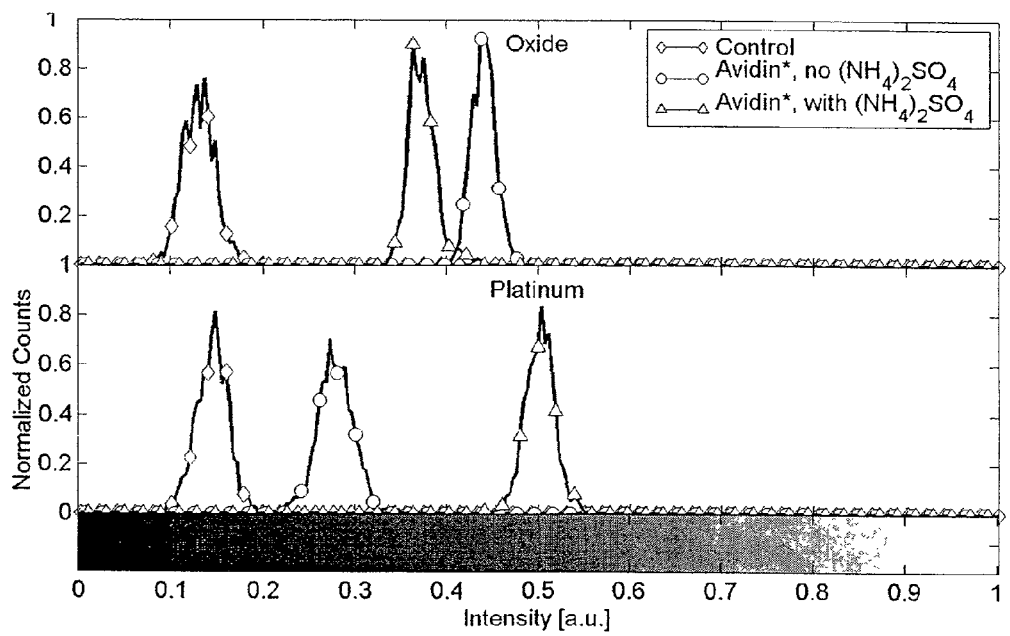
FIG. 16 is a pair of histogram graphs plotting fluorescence emission from surfaces of biochips, where a first boichip was unprocessed, a second boichip was processed for avidin adsorption at 37° C. for 15 hours without ammonium sulfate, and a third boichip was processed for avidin adsorption at 37° C. for 15 hours with ammonium sulfate. Histogram data labeled "control" correspond to untreated surfaces.

Another experiment showed that protein deposition on the boichip 20, 220 is enhanced when avidin is adsorbed from an ammonium sulfate solution. In this experiment, a chip was added to avidin solution (1 mg/mL) that had been previously mixed with ammonium sulfate to give a final concentration of 50% of ammonium sulfate. The chip and avidin solution was mixed gently in a vial, and incubated on ice for 30 minutes. The vial was then stored at 37° C. for 15 hours followed by washing of the chip in PBS. FIG. 16 shows the histograms of the emission intensity. The precipitation process induced by ammonium sulfate enhanced the deposition of avidin on platinum. The ammonium sulfate promotes a greater degree of adsorption of avidin on platinum (lower graph, triangles). The opposite effect is noted for the oxide (upper graph, triangles) (FIG. 16).

A possible explanation for the enhanced protein adsorption relates to the position of the ammonium sulfate, $(NH_4)_2SO_4$, on the lytotropic series. It is a kosmotrope and hence promotes an ordered arrangement of water molecules around itself and attracts water molecules away from the hydration layer that surrounds a protein in aqueous solution. The water layer around a protein helps to keep it in solution. The decrease in the water layer, such as happens in the presence of ammonium sulfate, promotes hydrophobic interactions between protein molecules and leads to their reversible aggregation and precipitation. This rationale led to the experiment where ammonium sulfate was added to the PBS in order to promote precipitation of avidin on surface of boichip 20, 220 by producing a concentrated protein layer near the surface. Such a layer was expected to enhance the adsorption of the protein onto the surface. This is confirmed by the experimental results graphed in FIG. 16. That drawing figure shows that adsorption of avidin onto platinum is greater in the presence of the ammonium sulfate than in the absence of this salt. The opposite effect is noted for the oxide layer, but the difference is not as pronounced as the enhanced adsorption on the platinum. This effect may reflect a difference in contact angles or surface tension of the oxide compared to the platinum.

Figure 17:
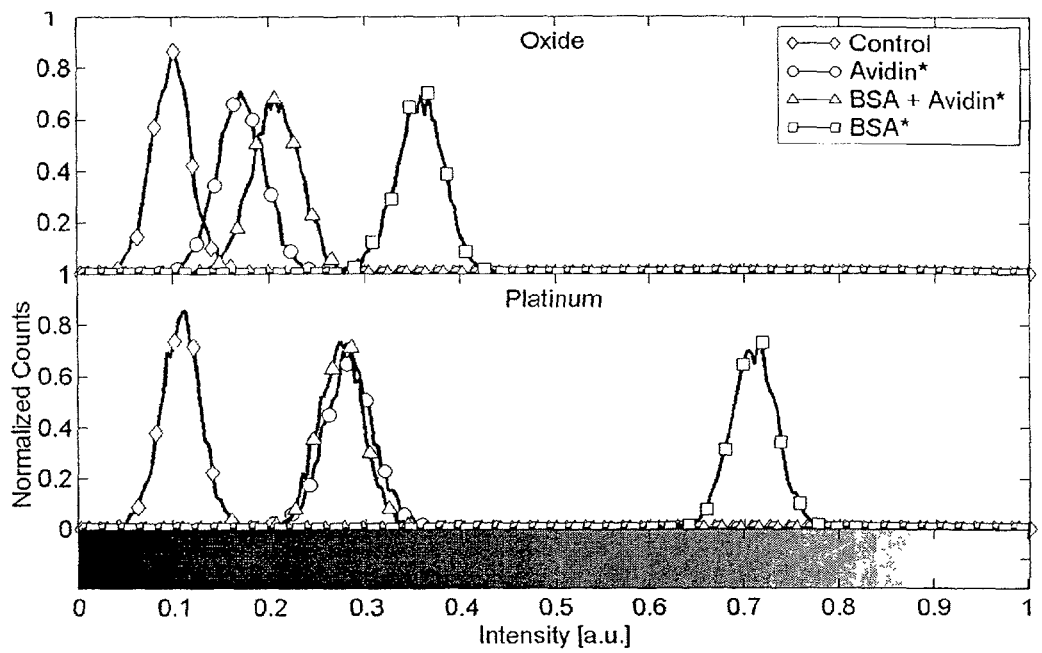
FIG. 17 is a pair of histogram graphs plotting fluorescence emission from surfaces of biochips, where a first biochip was unprocessed, a second boichip was treated with labeled avidin, a third boichip was treated with unlabeled BSA and labeled avidin, and a fourth biochip was treated with labeled BSA.
Figure 18:
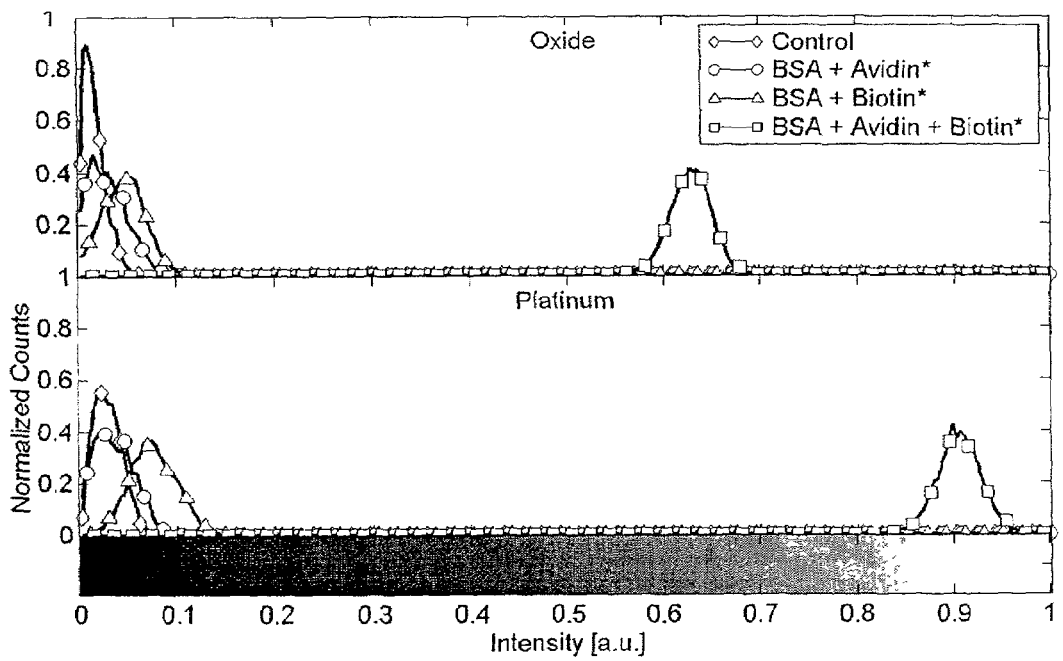
FIG. 18 is a pair of histogram graphs plotting fluorescence emission from surfaces of a reference boichip that was not contacted with any protein solution, a second boichip contacted with BSA and labeled avidin, a third boichip contacted with BSA and labeled biotin, and a fourth boichip contacted with BSA followed by unlabeled avidin and labeled biotin, as indicated.

The hypothesis that BSA (bovine serum albumin) might preferentially bind onto the oxide surfaces 54 (FIGS. 5A-5F) of boichip 20, 220 and thereby decrease adsorption of avidin on the oxide led to experiments where microscale biochips 20, 220 were incubated in a PBS buffer that contained BSA. The rationale was to direct binding of avidin onto the platinum surfaces of the electrodes 36 by blocking other sites on the chips using a second protein, such as BSA. Crystallized unlabeled BSA (Pierce, Cat. #77110, Lot #AD40111) and Fluorescein-labeled BSA (Pierce, Cat. #A-9771, Lot #89H7613) were purchased and dissolved in PBS to a concentration of 10 mg/ml. The chips were incubated in the BSA solutions at 40° C. for 2 hours. After the incubations, the chips were rinsed 3 times for 5 minutes each in PBS to remove excess unbound proteins. The chip was then stored wet at 4° C. for 15 hours before they were examined using fluorescence microscopy. The histograms generated from the resulting micrographs showed that more BSA binds onto the platinum than the oxide (compare peaks, squares, on lower and upper scales, respectively in FIG. 17). Furthermore, BSA binds to a greater extent than the avidin on both the oxide and platinum surfaces (FIG. 18). Avidin alone and BSA with avidin show similar emission and intensity peaks relative to each other (circles and triangles in lower scale of FIG. 18). Avidin binds to the surfaces on chips that have previously been treated with BSA. The BSA did not exhibit the postulated blocking effect. To the contrary, the data indicate that BSA unexpectedly promotes greater adsorption of the avidin onto the platinum surface and/or interacts with avidin in a manner that increases the intensity of fluorescence emission when avidin binds biotin (compare FIGS. 17 and 18).

The avidin itself maintains an active conformation on the surface of the chip. The avidin binds its target molecule (i.e., biotin) as indicated by the fluorescent signal obtained when labeled biotin is added to a chip that has previously been treated with unlabeled avidin, or unlabeled avidin and BSA. A chip treated with unlabeled BSA, then unlabeled avidin and finally fluorescein labeled biotin (FIG. 18) gave an emission brighter than that for an experiment where only unlabeled avidin (no BSA) was adsorbed onto the chip followed by addition of labeled biotin (data not shown).

The confirmation of avidin adsorption, and its ability to bind biotin, provides a method for fixing a primary antibody, specific for *Listeria monocytogenes*, onto boichip 20,220 by forming a biotinylated antibody. The biotin associated with the primary antibody protein binds with the avidin, already fixed onto the chip's surface (on electrodes 36 and oxide surfaces 54), and thereby anchors the antibody to which it is attached to the chip's surfaces. This type of approach is used in the preparation of particulate supports for affinity chromatography, and provides a viable option for biochips as well.

It is possible in some applications to have a selected antibody directly adsorbed on the boichip rather than anchoring it indirectly through avidin. For instance, the antibody Mab C11E9, Lot # 00614. Secondary antibodies (KPL, Cat. # 02-18-06, fluorescein-labeled antibody to mouse IgG (H+L) produced in goat, and negative antibody, FITC-conjugated goat F(ab)2 anti-human immunoglobulin-polyvalent). Binding can be determined by visual interpretation of fluorescence micrographs of emission patterns of labeled antibodies or cells.

In the above-described experiments, in the case of primary antibody, a volume of 10 μL of the primary antibody was pipetted onto the chip and then incubated for 30 min at 37° C. The antibody solution was recovered from the chip's surface so that it could be reused. (Only a fraction of the protein was expected to adsorb). Subsequent contact of bacteria or antibody with the chip was carried out after the chip had been washed twice with 100 μL of 0.05% Tween in PBS. The cells were FTIC labeled and diluted to about $10^6$ cells per mL before 100 μL of the cell suspension was pipetted onto the chip. Secondary antibodies were used to determine whether the primary antibody adsorbed on chips that had previously been treated with BSA. The experiments were designed to answer the following questions:

1. Does BSA blocking prevent the binding of bacteria to the chip's surface?
2. Does the primary antibody stick to the chip?
3. Does primary antibody on the chip bind heat-killed *Listeria monocytogenes*?

Incubation of the chips with BSA, primary antibody, and/or living and heat-killed bacteria, gave the answers to these questions. In the case of the bacterial binding, the numbers of bacteria that bound from one region to the next varied, although the patterns observed were sufficiently pronounced to interpret the micrographs with respect to any differences that may have resulted from different adsorption conditions. The data indicate that biochips treated only with buffer adsorb more heat-killed (at 80° C. for 20 min) *Listeria monocytogenes* on platinum than on oxide surfaces. *E. coli* cells do not show significant adsorption.

It was demonstrated by these experiments that BSA adsorbed on the chips reduces the already low level of *E. coli* binding but actually increases *Listeria monocytogenes* binding for *Listeria monocytogenes*. If BSA binds *Listeria monocytogenes*, then a larger population of *Listeria monocytogenes* should adsorb onto the platinum squares since BSA exhibits greater adsorption on platinum relative to oxide surfaces (FIG. 17). However, the image of distribution of beat-killed *Listeria monocytogenes* does not show such a pattern. These results are significant since they show that platinum has an affinity for *Listeria monocytogenes*, over *E. coli*, and BSA deposited on the surface of the chip further enhances the selectivity of the chip for one type of bacteria over another, even in the absence of the primary antibody. While an antibody is still needed as the bio-recognition element, selective materials design of the chip enhances the signal to noise ratio, if the chip's surface has lower affinity for non-pathogenic bacteria compared to pathogenic ones. In some applications, this design may or may not require deposition of a protein such as BSA.

It was additionally demonstrated by these experiments that the primary antibody binds to the chip, with preference indicated for platinum surfaces. The fluorescent pattern results when unlabeled primary antibody is adsorbed, followed by a labeled secondary antibody that binds to the primary antibody. In comparison, there is little fluorescence detected for a chip that has been treated with buffer (rather than primary antibody) followed by BSA and the secondary antibody. An analogous result is obtained for primary antibody adsorption followed by buffer wash. Buffer followed by a secondary antibody gives no emission. BSA has no discernible effect on blocking binding.

The monoclonal antibody MAb C11E9 binds with *L. monocytogenes* but also show some cross-reaction with some strains of *Listeria innocua*. Antigens that bind with this MAb are the 52, 55, 66, and 76 kDa surface proteins of the IgG2b subclass. A second antibody, Mab EM-7G1 binds with *L. monocytogenes*, and specifically with a 66 kDa surface protein (IG1 subclass). Despite the lower specificity of C11E9, its binding activity is attractive, since the antibody differentiates between living and dead cells.

Microwicking as Delivery Mechanism

Figure 19:
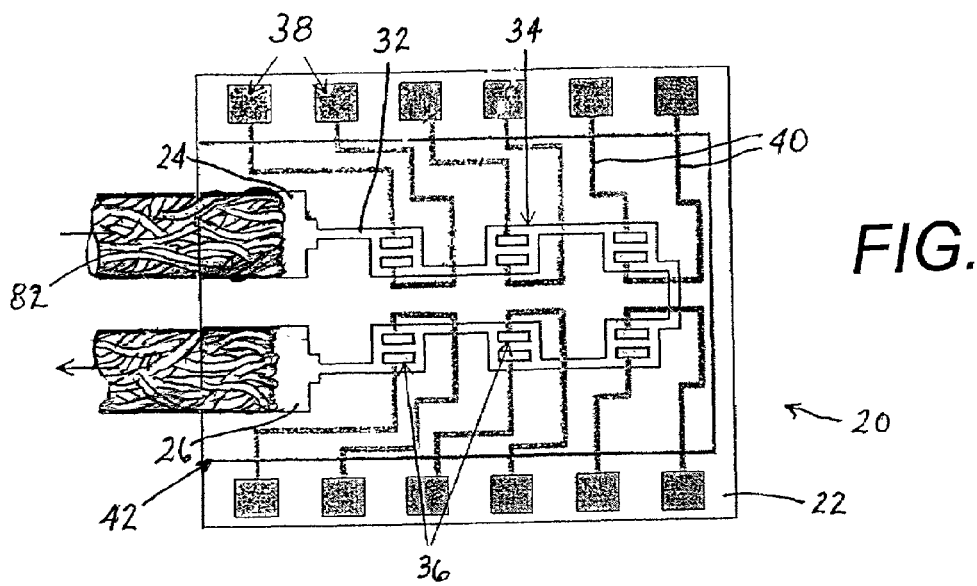
FIG. 19 is a schematic cross-sectional view of an alternative boichip design.

As depicted in FIG. 19, transporting of a fluid sample from a food product specimen to the boichip 20,220 may be implemented via a microfiber wick 82 taking the place of microbore tube 28 (FIG. 1). Experiments have shown that fluids can be transported for 2-cm distances in less than 3 minutes through such a microfiber wick 82. Wick 82 is approximately 20 to 100 microns in diameter. Preliminary experiments consisted of threading the wicks through pH paper and then holding the wicks vertically while they were placed in an acid solution. Transport of the fluid to the pH paper was indicated by a change in color of the paper. Tested materials were: (1) Zwicky-Trys 1189 100/3 Spun-Polyester (pink); (2) WoolyNylon 1000 m, YLI Corp 161W, Nylon 100% #283 (red); (3) 001 Richardson Silk A (light brown); (4) 100% polyester (light brown); (5) 100% Spun Polyester 0001 (white); and (6) Super Sheen, mercerized, 40 (white). The times required for the transport of the fluids through the wicks of the indicated lengths were: (1) 3 minutes/2 cm; (2) 5 hours/0.5 cm; (3) 45 seconds/2 cm; (4) 1 minute/2 cm; (5) 1 minute/2 cm; and (6) 45 seconds/2 cm.

Wick 82 may be placed inside of a support tube 84 as shown in FIG. 19. The utilization of microwick 82 instead of microbore tube 28 for transporting the fluid sample is attractive since there are no moving parts or mechanical energy needed to deliver the sample. This methodology would not be feasible for laboratory scale assays, but is attractive for a biochip, since the samples that must be delivered to the sensor are preferably less than about 100 microliters and more preferably less than 1 microliter. The channels 32, 212, 218 in the biochips 20, 220 are small (on the order of 100 microns), and hence diffusive transport at the chip surfaces will be a controlling parameter.

Additional Bioseparation Mechanisms

Figure 20:
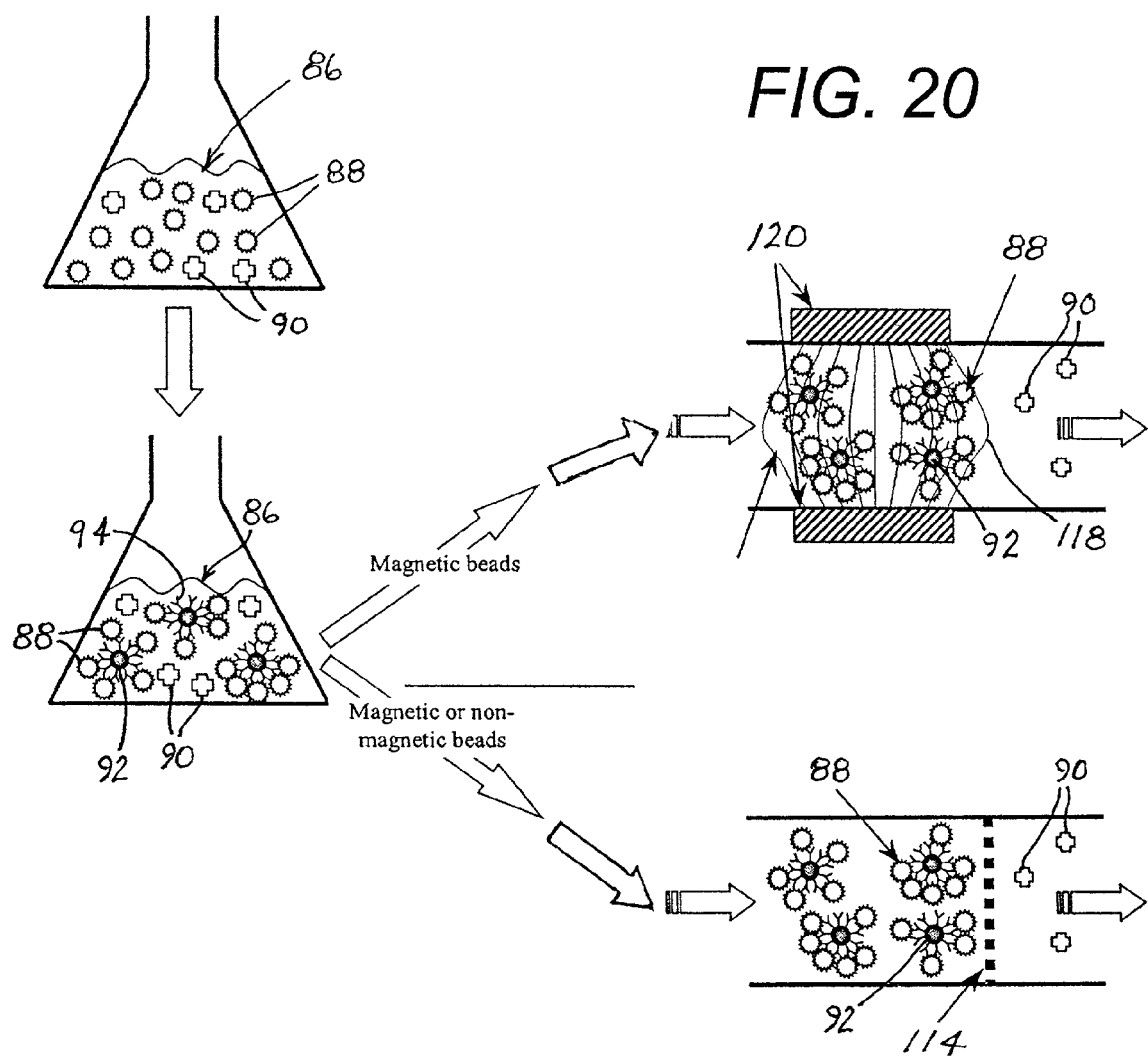
FIG. 20 is a diagram illustrating steps in a bioseparation procedure utilized in a biodection process in accordance with the present invention.

An additional or alternative bioseparations method will now be described with reference to FIG. 20. A fluid sample 86 taken from bodily fluids, foodstuffs, soil, etc., contains live microorganisms 88 such as bacteria or single-cell fungi. The sample also contains contaminant biological matter or detritus 90, that is, biological material which is not targeted by the detection process. Such biological material includes protein molecules and non-pathogenic cells, as well as molecular and cellular fragments.

Figure 21:
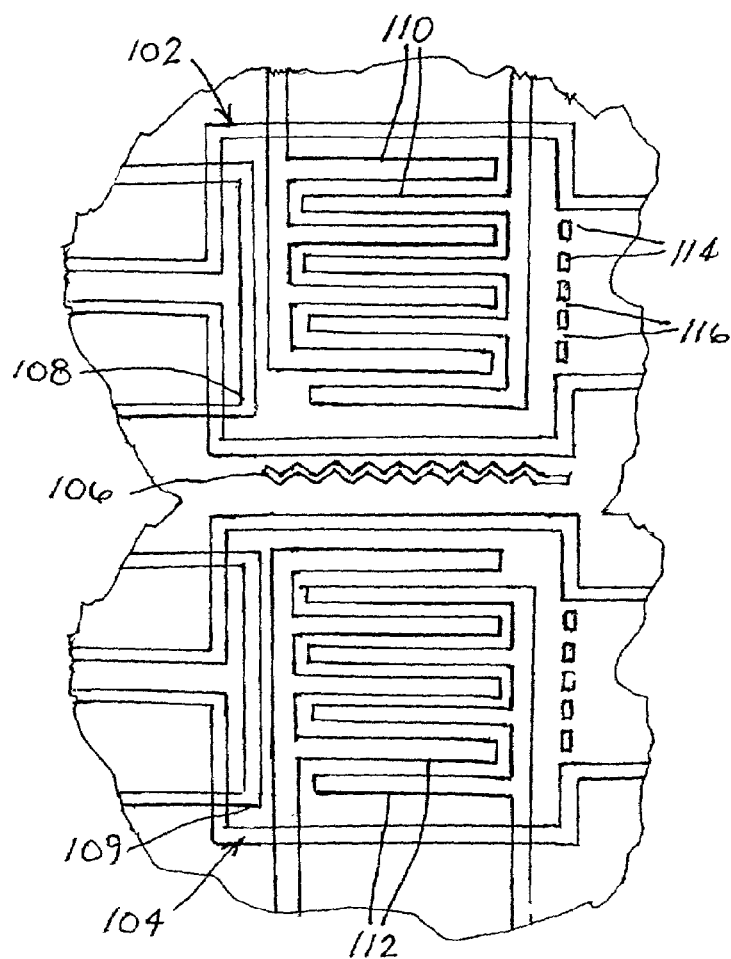
FIG. 21 is a partial schematic top plan view of a biosensor or biochip, showing a detection chamber with interdigitated electrodes, heating element and temperature sensor.

The present electronic method using boichip 20 or 220 is based on the confinement of a small number (1 to 1000) of the microorganism or microorganisms 88 of interest into a very small volume, on the order of 1 picoliter to 1 microliter, and measuring the changes in the electrical characteristics of the fluid in which the microorganisms are suspended. These changes are produced by the release of byproducts of the microorganism's metabolism into the fluid (mainly by the ionic species released). The microorganisms 88 may be selectively collected from the raw sample 86 by means of beads or microspheres or beads 92 functionalized with antibodies 94 specific to the microorganism of interest, affinity chromatography (also using antibodies), filtration using synthetic or natural membranes, or any other technique than can selectively and controllably separate and concentrate some of the microorganisms from the original sample. After collection, the microorganisms are suspended in a liquid medium having a low conductivity (lower than 100 gS/cm), such as Tris-Glycine buffer (3.6 mM Tris, 4.7 mM Glycine). To this medium, a single or multiple non ionic nutrients, such as a sugars, and enough dissolved oxygen (in the case of aerobic microorganisms) are added to stimulate bacterial metabolism. These nutrients can be selected such that they can be more easily metabolized by the microorganism of interest, than by other microorganisms that might be present due to inefficiencies in the selective collection method used. In this way, the selectivity can be increased beyond what the collection step provides. After the microorganisms are suspended in the low conductivity medium, they are injected into a container 102 (FIG. 21) which may take the form of detection chamber or cavity 34 (FIG. 1) or 204, 206 (FIG. 2) with a volume between 1 picoliter and 1 microliter. At the same time, a sample of low conductivity medium with nutrients but no microorganisms, is injected into another container 104 (FIG. 21), identical to the first one. Some means of heating the containers 102 and 104 and controlling their temperature should be provided, such that the temperatures of the two containers do not differ by more than ±0.1° C. The preferred but not exclusive way of accomplishing this is by having the containers in very close physical contact. A pair of metallic electrodes 110, 112 are either suspended in each container 102, 104, or attached to the walls thereof, with the electrodes 110 in one container 102 being identical in structure and composition to those 112 in the other container 104. The preferred form of these electrodes is an interdigitated structure.

After injection of the samples into the test containers, the temperature of the containers is raised to a level that will stimulate the metabolism of the microorganisms and maintained at that level for several hours. While the samples are at this temperature, the AC electrical impedance of the electrodes in each container is repeatedly measured at several frequencies, between 100 Hz and 1 MHz, at time intervals on the order of minutes. A circuit model of the electrode-liquid medium-electrode system is fitted to the resulting frequency vs. impedance curves to extract the parameters of the model. As the microorganisms metabolize the provided nutrients and release ionic species into the medium, the parameters of the model fitted to the curves measured at the container with bacteria change over time. At the same time, the parameters extracted from measuring the impedance of the electrodes in the container with no bacteria remain constant within the limits imposed by the noise inherent in the measurement, since no metabolic activity is taking place in this container. If a statistical analysis and comparison of the parameters extracted from measuring both containers indicates that their difference is statistically significant, it can be concluded that the bacteria present in the first container have been detected.

The vast majority of the bacterial detection methods currently in use are based on fluorescent tagging of the bacteria, or on the detection of DNA fragments from the bacterial genome. Both techniques are unable to determine if the microorganism was dead or alive in the original sample, and both require extensive manipulations of the sample. Moreover, any fluorescence technique requires bulky and expensive optical apparatuses for excitation and detection of the fluorescence. Additionally, when the microorganism is present in very small concentrations (10 to 1000 cells per milliliter), a growth step is necessary to increase the concentration, but this can drive the total assay time to anywhere from 2 to 7 days.

The present technique solves some of these problems. By its very nature, the technique described above inherently detects only live microorganisms, which is very important for certain applications, especially in food safety (many microorganisms present in food are not pathogenic if they are dead). It also relies exclusively on electrical signals, making the related equipment less expensive and smaller than others. Additionally, the absence of a growth step makes detection possible in a couple of hours instead of days.

Equipment for the analysis of the conductivity or impedance of an incubated bacterial suspension have been available for a number of years, but they suffer from two limitations. First, their selectivity is poor because they rely on the composition of the growth medium for encouraging the proliferation of the microorganism of interest, while suppressing the proliferation of others. The second limitation is related to the scale in which the assay is performed. The available equipment uses volumes of bacterial suspension in the milliliter range and above, which requires large numbers of bacteria to provide a discernible signal. The present technique utilizing boichip 20, 220 bypasses the first limitation by requiring a selective separation prior to the assay, and increases the sensitivity for very small numbers of microorganisms (1 to 1000) by confining them to an extremely small volume (1 picoliter to 1 microliter). Additionally, the present use of a low conductivity buffer increases even further the sensitivity. Since the ionic concentration of the low conductivity buffer is very low, even very small amounts of ions released by the microorganisms can produce a large change in impedance. In addition, measuring the impedance over a large range of frequencies (100 Hz to 1 MHz) and fitting a model circuit to the measurements also improves the sensitivity of the technique.

As discussed above, a detection device such as boichip 20 or 220 has two identical detection chambers or cavities 102, 104 with volumes between 1 picoliter and 1 microliter. Some means of heating the chambers 102, 104 and controlling their temperature may be provided, such that the temperatures of the two chambers do not differ by more than ±0.1° C. (the preferred but not exclusive way of accomplishing this is by having the chambers in very close physical contact). The temperature can be controlled by one or more resistive heaters 106 and temperature sensors 108, 109 micro fabricated within or adjacent to the detection chambers. A pair of metallic preferably interdigitated electrodes 110, 112 are either suspended in each chamber or cavity 102, 104 or attached to its walls, with the electrodes 110 in one chamber 102 being identical in structure and composition to those 112 in the other chamber 104. As further illustrated in FIG. 21, the chambers or cavities 102, 104 (or 34, 204, 206) are designed so that the antibody-functionalized microspheres or beads 92 (FIG. 20) can be trapped inside them, while allowing fluids to pass through. The beads 92 can be trapped by a micro fabricated filter-like structure 114 such as a grid or series of gating posts, with orifices or passages 116 large enough for non-target bacteria and other biological material 90 present in the injected sample to go through, but small enough to prevent the beads 92, with the attached target microorganisms 88 from flowing out. If the beads 92 are magnetic, a magnetic field 118 (FIG. 20) could be used to trap them inside the chamber, eliminating the need for the mentioned filter-like retention structure 114. The magnetic field 118 can be established by permanent magnets or electromagnets 120 micro fabricated within or adjacent to the detection chamber.

Microorganism collection can be performed in two slightly different ways, after the sample has been concentrated and cleaned to remove excess salt, food debris, and other unwanted material. Pursuant to the first technique, depicted in FIG. 20, the beads 92 are mixed with the sample 86 containing the microorganisms 88, outside of the measuring volume, and the antibodies 94 are allowed to capture the bacteria 88 for a specific period of time. This time should be long enough to allow the antibodies 94 on the beads 92 to capture all of the microorganisms 88 of interest that might exist in the sample 86. After capture, the beads 92 can be separated from the sample by filtration or magnetically (in the case of magnetic beads), and resuspended in a "washing" fluid to completely eliminate any unwanted material (unwanted microorganisms, food debris, excess salt, etc.) that might have been left after the initial cleaning step; this fluid can also help remove any species non-selectively bound to the antibodies. Subsequently, the beads 92 are injected into a detection chamber 102 and trapped there (along with the microorganisms 88 they carry) by magnetic field 118, in the case of magnetic beads 92, or by filter structure 114 previously described. Alternatively, the sample 86 plus beads 92 can be injected directly into the chamber 102 and the washing step could be performed after the beads have been trapped inside the chamber.

Figure 22:
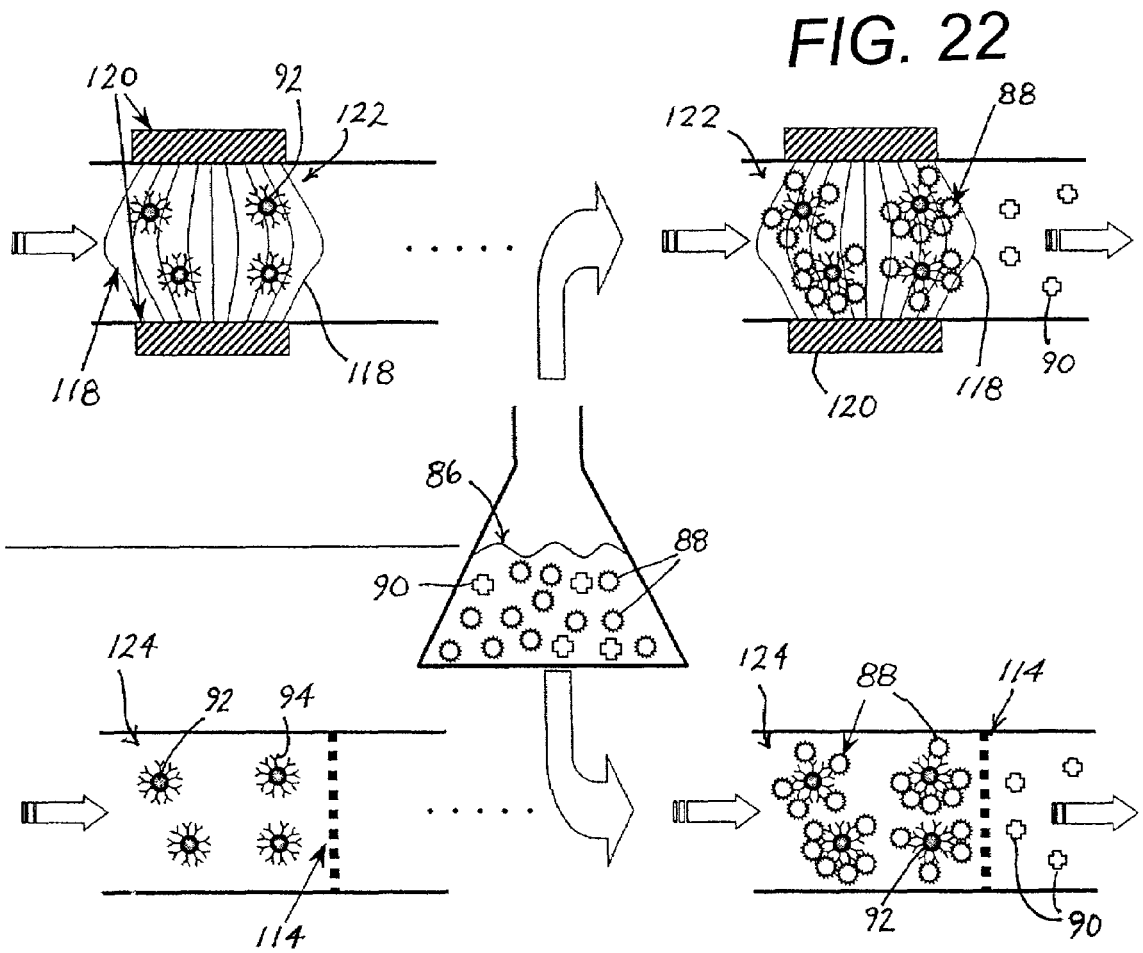
FIG. 22 is a diagram illustrating steps in another bioseparation procedure utilized in a biodetection process.

In another technique of microorganism collection, depicted in FIG. 22, the beads 92 are first injected into a detection or measuring chamber 122 or 124 and trapped there by magnetic field 118, in the case of magnetic beads 92, or by filter structure 114 described above. The sample 86 containing the microorganisms 88 (which could have been previously purified and concentrated) is then flowed through the chamber 122 or 124 containing the beads 92 at a rate that would allow for any and all of the microorganisms 88 of interest to be captured by the antibodies 94 on the beads. After capture, a "washing" fluid is passed through the chamber 102 to wash away, from the chamber and the beads 92, any unwanted material (unwanted microorganisms, food debris, excess salt, etc.) that might have been left after the initial cleaning step; this fluid can also help remove any species non-selectively bound to the antibodies. This second technique is similar to the principle of affinity chromatography, with the measuring chambers acting as chromatographic columns.

The collection step is performed for two samples 86 with two separate sets of beads 92, one set for each sample. One sample is the test sample being analyzed for the presence of microorganisms, the other is a "dummy" or reference sample, artificially prepared to ensure that it does not contain any microorganisms 88. Each set of beads 92 is injected into one of the chambers 102, 104 (or 122) in the detection device, and trapped there by the means described earlier. This results in one chamber 104 containing beads 92 that are guaranteed not to have any microorganisms 88 attached to them. This latter chamber may be called "the reference chamber," while the other chamber 102, which could have the microorganisms 88 of interest if they were present in the original sample, will be called "the detection chamber."

Once the beads 92 are trapped inside the chambers 102, 104 (or 122), the chambers are filled with a liquid medium having a low conductivity (lower than 100 gS/cm), such as Tris-Glycine buffer (0.2 mM Tris, 4.7 mM Glycine). This medium also contains a single or multiple nonionic nutrients, such as sugars, and enough dissolved oxygen (in the case of aerobic microorganisms) to stimulate the microorganism's metabolism. These nutrients can be selected such that they can be more easily metabolized by the microorganism of interest than by other microorganisms that might be present due to inefficiencies in the antibody-mediated capture. In this way, the selectivity can be increased beyond what the antibody-based collection step provides. After injection of the samples, the temperature of both chambers is raised to a level that will stimulate the metabolism of the microorganisms 88 and maintained at that level for several hours. While the samples are at this temperature, the AC electrical impedance of the electrodes 110, 112 in each chamber 102, 104 (or 122) is repeatedly measured at several frequencies, between 100 Hz and 1 MHz, at time intervals on the order of minutes. A computer, or microprocessor, or microcontroller, or digital signal processor acquires the measured impedance vs. frequency data and analyzes it to extract certain parameters that will be the basis for detection. If microorganisms 88 were captured by the beads 92 in the detection chamber 102 (122), the parameters extracted from the curves measured at the detection chamber change over time because the microorganisms metabolize the provided nutrients and release ionic species into the medium. These ionic species, in turn, change the electric properties of the liquid medium and hence change the impedance of the electrodes in contact with the liquid. At the same time, the parameters extracted from the impedance of the electrodes 112 in the reference chamber 104 remain constant within the limits imposed by the noise inherent in the measurement, since no metabolic activity is taking place in this chamber (it was guaranteed from the beginning that no bacteria would be present in the reference chamber). If a statistical analysis and comparison of the parameters extracted from measuring both chambers indicates that their difference is statistically significant after a suitable incubation time, it can be concluded that the microorganisms 88 present in the detection chamber 102 have been detected. If no organisms are present in the detection chamber, no statistically significant difference in the extracted parameters will be observed. Also, if the microorganism of interest is present but dead, no change will be detected. The electronic detection method has been tested experimentally, demonstrating that 50 bacteria cells (*Listeria innocua*) confined into a volume of 5.3 nanoliters produce a detectable change in the impedance of a low conductivity medium. According to the experimental data, the limit in sensitivity seems to be somewhere between 1 and 50 cells in a 5.3 nl volume.

There are a multitude of parameters that could be extracted from the measured impedance vs. frequency data. One possibility is to fit a circuit model of the electrode-liquid electrode system to the data (using a least squares method, for example) to obtain values for the components of the circuit model. All or some of these values can be used as the detection parameters. Another method involves using only the phase of the impedance phasor as the detection parameter. Experiments indicate that changes in the phase of the impedance, at selected frequencies, are good indicators of bacterial metabolism. Additionally, the phase of the impedance can be measured with very high precision much more easily than the magnitude. It could also be possible to achieve detection by a DC measurement of the resistivity of the liquid inside the chambers, instead of using an AC measurement. The resistivity can be measured by a four-point-probe method, using four electrodes laid out in a Van der Pauw geometry in each chamber, in place of one pair of interdigitated electrodes 110,112.

Alternative Detection Mechanisms

The sensing of a target microbiological species such as a pathogenic bacterium in a detection chamber or cavity 34, 204, 206 may be implemented via circuit designs other than electrodes 36 (110, 112). For instance, a binding agent such as an avidin-biotinylated antibody may be attached to a gate of a silicon MOSFET. The MOSFET is a charge sensor where charge changes induced on the gate by the coupling of a target microbiological species become mirrored in a channel region under the gate insulator. The device must be biased in the sub-threshold regime where the $dI/dV_G$ slope is the maximum, i.e., the drain to the source current ($I_{DS}$) is maximum as a function of voltage on the gate ($V_G$). The device can be biased in the appropriate regime using the back bias or a dual gated MOSFET where the threshold of the top gate is controlled by the bottom gate. The double layer interfacial capacitance changes with the binding of the antigen and the related conformation changes.

The simple MOSFET of this detection structure is fabricated in silicon. The device has gate oxides of less than 150 Å. Platinum is used as the gate material and the exposed gate area may vary from 100 µm×100 µm to 2 µm×2 µm. The fabrication of the MOSFET is standard and double gated MOSFETs may also be used. Each device has a source, drain and body terminal in addition to the open (exposed) gate terminal. The devices are packaged and biochemically treated with binding agents as described hereinabove. The main difference is that the measurement consists of source to drain current measured by a high-precision pico-ammeter, a semiconductor parameter analyzer, or a digital oscilloscope. The device is biased using a DC and AC signal and the measurements will be taken before, during and after the binding of the avidin to the biotinylated gate electrode. Only the binding event taking place on the gate electrode affects the source/drain current measurement.

Alternative Collection Procedures

As discussed hereinafter with references to FIGS. 23-25, microorganism collection can be performed in two main ways, after the sample has been concentrated and cleaned to remove excess salt, food debris, and other unwanted material.

Figure 23:
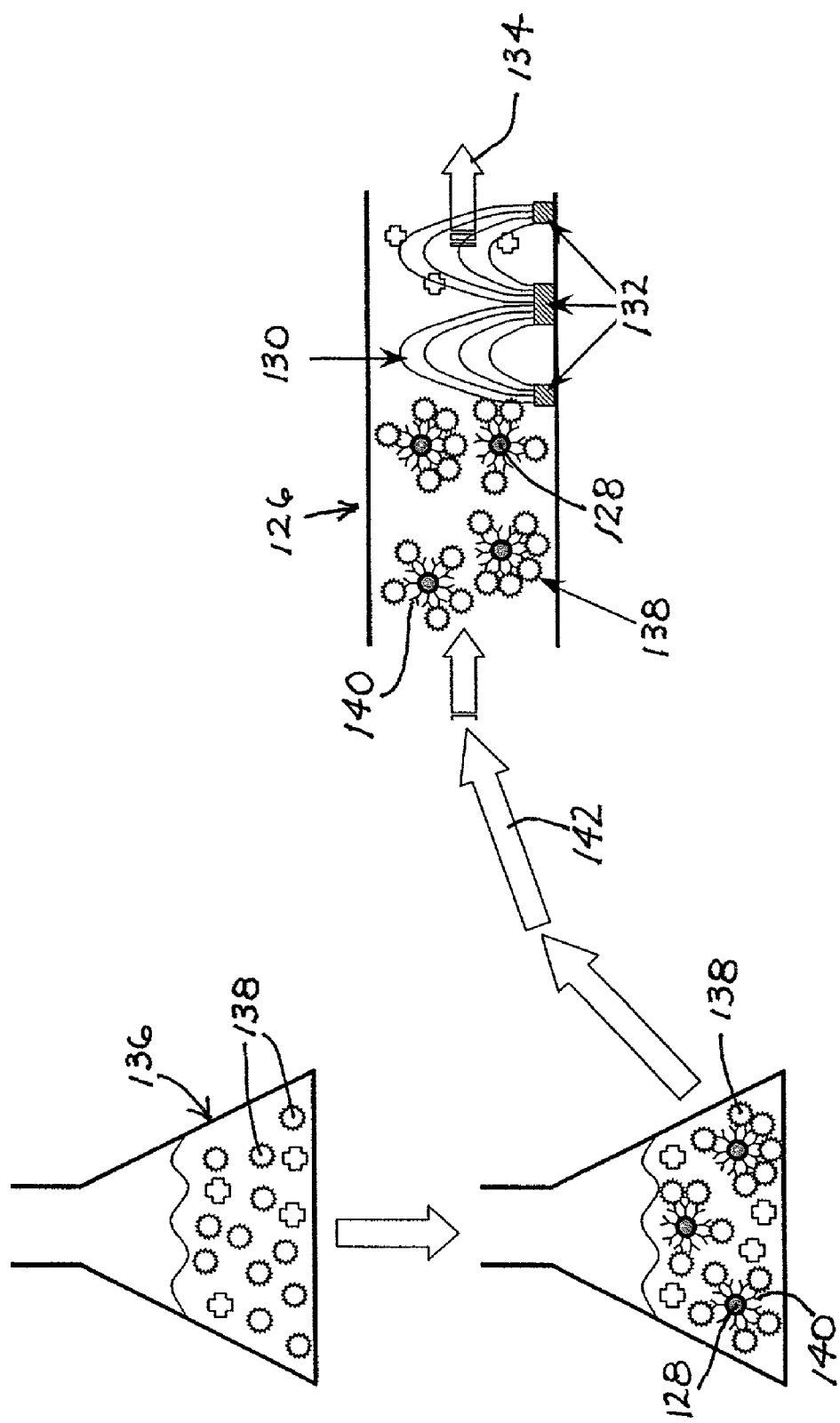
FIG. 23 is a diagram illustrating successive steps in a bioseparation portion of an organism detection process, in accordance with the present invention.

For the first collection method, a detection/collection chamber 126 (FIG. 23) is designed so that antibody-functionalized beads 128 can be trapped or collected inside, while allowing fluids to pass through. This entrapment or capture is effectuated through the use of dielectrophoresis (DEP). In this approach, a non-uniform AC electric field 130 is established within the chamber 126 or at its output, by either additional electrodes 132, or the same electrodes (e.g., 36) used for measuring the metabolic activity. In either case, the electrodes have a different geometry (size, shape) so that the non-uniform electric field 130 will be generated. The frequency of the field 130 and the material of the beads 128 (insulating with a dielectric constant much lower than that of water, such as polystyrene, latex, etc.) are chosen so that the beads are repelled from the regions where the gradient of the RMS (root mean square) value of the field is maximum (negative DEP). The geometry and magnitude of the field are designed so that this repulsive DEP force will retain the beads 128 against the drag force exerted by the fluid 134 flowing around them. The DEP-mediated capture of beads 128 can be exploited in two different ways:

In a first method for capturing beads 128, shown in FIG. 23, the beads are mixed with a pre-cleaned and concentrated sample 136 containing microorganisms 138 of interest, outside of the measuring volume, and antibodies 140 on beads 128 are allowed to capture the bacteria 138 for a specific period of time. This time should be long enough to allow the antibodies 140 to capture all of the target microorganisms 138 that might exist in the sample 136. After capture, the beads 128 can be separated from the sample 136 by filtration, or centrifugation, or magnetically (using magnetic beads), and resuspended in a "washing" fluid to completely eliminate any unwanted material (unwanted microorganisms, food debris, excess salt, etc.) that might have been left after the initial cleaning step; this fluid can also help remove any species non-selectively bound to the antibodies. Subsequently, the beads 128 are injected into the detection chamber 126 in a step 142 and trapped there (along with the microorganisms 138 they carry) by the DEP force arising from field 130. Alternatively, the sample 136 including beads 128 can be injected directly into the detection chamber 126, and the washing step could be performed after the beads have been trapped inside the chamber.

Figure 24:
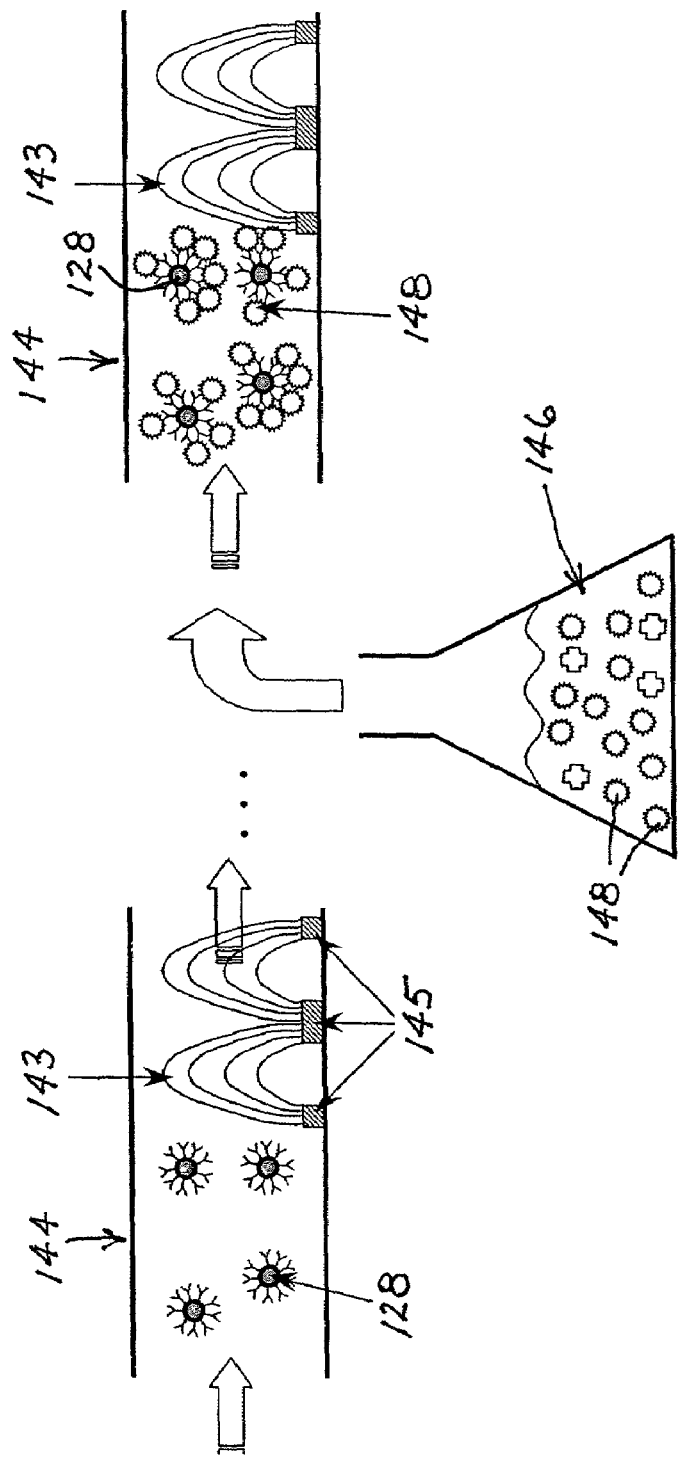
FIG. 24 is a diagram illustrating successive steps in another bioseparation procedure of an organism detection process, in accordance with the present invention.

In a second method for capturing beads 128, depicted schematically in FIG. 24, the beads 128 are first injected into a detection/collection chamber 144 and collected there by a dielectrophoresis field 143 generated by differently sized and/or differently shaped electrodes 145 as described above. A sample 146 containing microorganisms 148 of interest (which could have been previously purified and concentrated) is then flowed through the chamber 144 containing the beads 128 at a rate that would allow for any and all of the microorganisms 148 of interest to be captured by the antibodies 140 provided on the beads. After capture, a "washing" fluid is passed through the chamber 144 to wash away, from the chamber and the beads 128, any unwanted material (unwanted microorganisms, food debris, excess salt, etc.) that might have been left after the initial cleaning step; this fluid can also help remove any species non-selectively bound to the antibodies. This second method is similar to the principle of affinity chromatography, with the measuring chambers acting as chromatographic columns.

Figure 25:
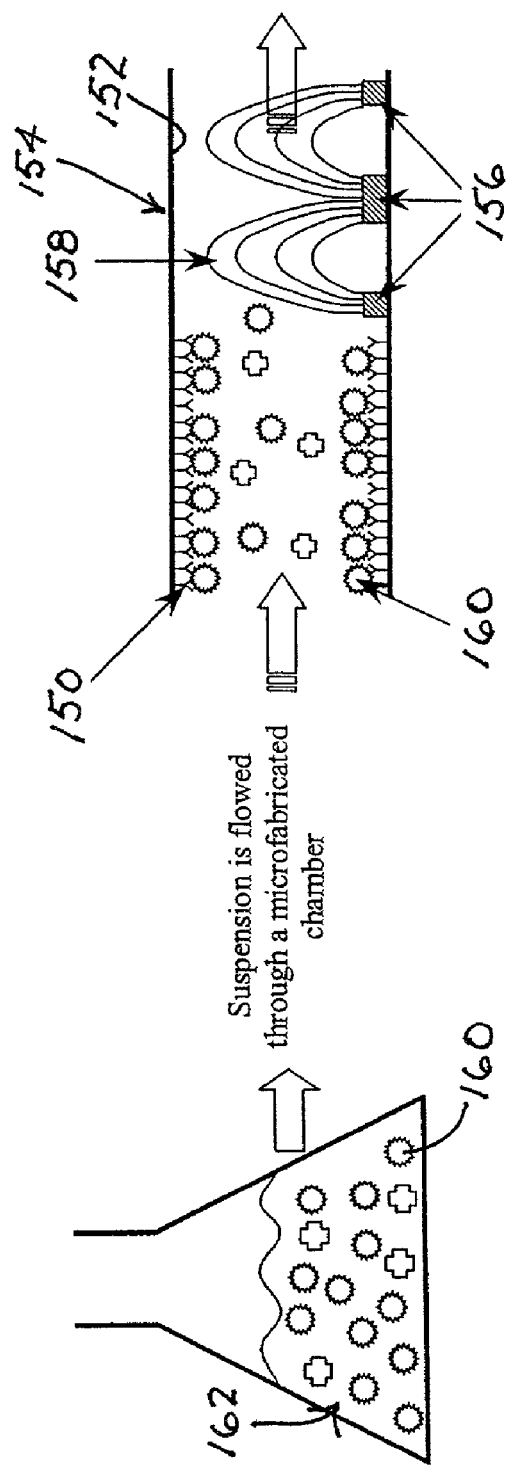
FIG. 25 is a diagram illustrating successive steps in yet another bioseparation procedure of an organism detection process, in accordance with the present invention.

The second collection method, illustrated diagrammatically in FIG. 25, requires the immobilization of antibodies 150 onto inner surfaces 152 of a detection chamber 154 where microorganisms are collected and measurements are made. A set of electrodes 156 is fabricated within the detection/collection chamber 154 for implementing the dielectrophoretic capture of bacteria. The frequency and magnitude of an alternating electric field 158 produced by the electrodes 156, together with the conductivity of the carrier medium, are chosen so that the microorganisms 160 of interest are retained inside the chamber 154 by the DEP force (in the same way as beads 128 were retained in the previous capture method). After a sample 162 that is to be analyzed for the presence of the target microorganisms 160 is cleaned and concentrated, it is injected into the measuring chamber 154, where the DEP field 158 is created by electrodes 156. As the sample 162 flows through the chamber 154, the target microorganisms 160 are retained inside the chamber 154 by the DEP force. The DEP field 158 is maintained for a time long enough for the target microorganisms 160 to be captured by the antibodies 150 that are immobilized inside the chamber 154. The DEP force may not be selective enough to retain exclusively the target microorganisms 160, so other kinds of microorganisms are also retained by it; but the immobilized antibodies 150 capture only the desired microorganisms 160. After a period of time long enough to flow the whole sample 162 through the chamber 154 and to guarantee the antibody-based capture, the DEP field 158 is turned off and a washing solution is flowed through the chamber to remove any non-specifically bound species.

The DEP electric field may be applied periodically, in a pulsed mode. The microbiological entity of interest is attached to internal surfaces of chamber 154 (to the fixed or permanent walls thereof, to electrodes 156, via antibodies and/or by carrier elements such as microspheres) during intervals of application of the DEP field. At least some contaminants are removed from the fluid sample in chamber 154 during periods between successive intervals of application of the DEP field. This removal is effectuated by flowing the fluid sample through and out of chamber 154.

It is to be noted that FIG. 25 depicts a continuous flow method, at least prior to the deactivation of the DEP field 158. The microorganisms of interest are sequestered by the dielectrophoretic field, which increases the probability of contact of the microorganisms with antibodies 150. (In a laminar flow situation, the microorganisms are not likely to get close enough to the antibodies 150 to enable capture thereby.)

The collection step is performed for two samples. One sample 136, 146, 162 is the real one being tested for the presence of microorganisms 138, 148, 160, while the other is a "dummy" or reference sample. The reference sample is prepared from the same specimen as the test sample and has the same constituents except for the microorganisms. The microorganisms may be removed via a filtration process implemented via a mechanical filter such as a micro fabricated grating or via a DEP field. As discussed above, a DEP field may be used to filter the microorganisms from a continuous stream of a carrier fluid. The carrier fluid passing through the dielectrophoresis chamber prior to the deactivation of the field is routed to the reference chamber, while the fluid with microorganisms released by deactivation of the DEP field is directed to a detection chamber.

Each test sample 136, 146, 162 is injected into a respective detection chamber 126, 144, 154 in the detection device, and the microorganisms trapped there by dielectrophoresis as described above. Each reference sample (not separately shown) is injected into a respective reference chamber (not shown in FIGS. 23-25). This results in one chamber containing antibodies that are guaranteed not to have any microorganisms attached to them.

Detection chambers 126, 144, and 154 have inlet channels and outlet channels, as discussed above, and are manufactured as described hereinabove with references to FIGS. 5A-5F. Once the microorganisms 138, 148, 160 are trapped inside the detection chambers 126, 144, 154 (by the means described above), both the detection chambers and the reference chambers are filled with a liquid medium having the minimum amount of nutrients, and enough dissolved oxygen (in the case of aerobic microorganisms) to stimulate the microorganism's metabolism. These nutrients can be selected so that they can be more easily metabolized by the target microorganism 138, 148, 160 than by other microorganisms that might be present due to inefficiencies in the antibody-mediated capture. In this way, the selectivity can be increased beyond what the antibody-based collection provides.

After injecting the samples, the temperature of both the detection chamber 126, 144, 154 and the reference chamber is raised to a level that will stimulate the metabolism of the microorganisms 138, 148, 160 and maintained at that level for several hours. While the samples are at this temperature, the AC electrical impedance of measurement electrodes in each chamber is repeatedly measured at several frequencies, between 100 Hz and 1 MHz, at time intervals on the order of minutes. (The measurement electrodes may be separate electrodes, e.g., 36 in FIG. 1 et seq., or the same electrodes 132, 156 as used to generate the dielectrophoresis field.)

A computer, or microprocessor, or microcontroller, or digital signal processor (not shown) acquires the measured impedance vs. frequency data and analyzes it to extract certain parameters that will be the basis for detection. If microorganisms 138, 148, 160 were captured by the beads 128 in the detection chamber 126, 144, the parameters extracted from the curves measured at the detection chamber change over time because the microorganisms metabolize the provided nutrients and release ionic species into the medium. These ionic species, in turn, change the electric properties of the liquid medium and hence change the impedance of the measurement electrodes, which are in contact with the liquid. At the same time, the parameters extracted from the impedance of the measurement electrodes in the reference chamber remain constant within the limits imposed by the noise inherent in the measurement, since no metabolic activity is taking place in this chamber (no bacteria is present in the reference chamber). If a statistical analysis and comparison of the parameters extracted from measuring both the detection chamber 126, 144, 154 and the reference chamber indicates that their difference is statistically significant after a suitable incubation time, it can be concluded that the microorganisms 138, 148, 160 present in the detection chamber 126, 144, 154 have been detected. If no organisms are present in the detection chamber 126, 144, 154, no statistically significant difference in the extracted parameters will be observed. Also, if the target microrganism 138, 148, 160 is present but dead, no change or a very small change will be detected. And even if dead cells produce a relatively large change, the shape of the change over time will be different from that produced by live cells. Such differences in shape could be used to distinguish dead cells from live ones.

The electronic detection method has been tested experimentally, demonstrating that 50 bacterial cells (*Listeria innocua*) confined into a volume of 5.3 nanoliters produce a detectable change in the impedance of both a low and a medium conductivity medium. According to the experimental data collected up to now, the limit in sensitivity seems to be somewhere between 1 and 50 cells in a 5.3 nl volume.

There are a multitude of parameters that could be extracted from the measured impedance vs. frequency data. One possibility is to fit a circuit model of the electrode-liquid-electrode system to the data (using a least squares method, for example) to obtain values for the components of the circuit model. All or some of these values can be used as the detection parameters. Another method would involve using only the phase of the impedance as the detection parameter. Experiments indicate that changes in the phase of the impedance, at selected frequencies, are good indicators of bacterial metabolism. Additionally, the phase of the impedance can be measured with very high precision much more easily than the magnitude.

It is also possible to achieve detection by a DC measurement of the conductivity of the liquid inside the chambers, instead of using the AC measurement described above. The conductivity can be measured by a four-point-probe method, using four electrodes laid out in a Van-der-Pauw geometry in each chamber, in place of one pair of interdigitated electrodes. There are also two-probe techniques that can be used to measure the conductivity with high accuracy.

Although the invention has been described in terms of particular embodiments and applications, one of ordinary skill in the art, in light of this teaching, can generate additional embodiments and modifications without departing from the spirit of or exceeding the scope of the claimed invention. For example, the substrate of a boichip may be of a material other than silicon, including but not limited to glass such as Corning 7740, and polymers such as polyethylene based plastics and polytetrafluoroethylene.

It is to be noted that other methods of measuring electrical conductivity equivalent to the methods detailed herein may be used to detect the presence of a target microbiological species inside a microscale biochip. For instance, the bulk solution resistance $R_S$ may be determined directly using a four point probe sheet resistivity measurement. In this technique, four electrodes are positioned in a detection chamber at corners of a quadrilateral such as a square. Current is conducted between two diagonally opposed electrodes, while voltage is measured across the other two diagonally disposed electrodes. The interfacial impedance $Z_w$ is automatically eliminated.

Accordingly, it is to be understood that the drawings and descriptions herein are proffered by way of example to facilitate comprehension of the invention and should not be construed to limit the scope thereof.

What is claimed is:

1. A method for collecting and rapidly concentrating a microbiological substance, comprising:
   providing a microfabricated boichip having a collection chamber;
   delivering a fluid sample to said collection chamber in said biochip, said fluid sample containing a microbiological entity of interest;
   generating a spatially non-uniform electric field in said collection chamber in a pulsed mode so that successive intervals of application of said non-uniform electric field are spaced from one another by periods of time;
   retaining said microbiological entity of interest in said collection chamber during the successive intervals of application of said non-urn form electric field at least partially by virtue of said non-uniform electric field; and
   retaining said microbiological entity of interest in said collection chamber during said periods of time.

2. The method defined in claim 1,:
   wherein the retaining of said microbiological entity of interest in said collection chamber during said periods of time is accomplished by attaching said microbiological entity of interest to said collection chamber during said intervals of application of said non-uniform electric field, further comprising:
   removing at least some contaminants from said fluid sample in said collection chamber during said periods between successive intervals of application of said non-uniform electric field while retaining said microbiological entity of interest in said collection chamber during the successive intervals of application of said non-uniform electric field and during said periods of time, the removing of said contaminants being performed by flowing said fluid sample out of said chamber.

3. The method defined in claim 2 wherein attaching said microbiological entity of interest to said collection chamber includes attaching antibodies to at least one fixed or permanent surface of said collection chamber and attaching said microbiological entity of interest to said surface via said antibodies.

4. The method defined in claim 1 wherein the retaining of said microbiological entity of interest in said collection chamber includes adding to said fluid sample, prior to the delivering thereof to said collection chamber, a plurality of microscopic carrier elements each provided with a multiplicity of binding agents for. coupling said microbiological material to said carrier elements.

5. The method defined in claim 4 wherein said carrier elements are beads or microspheres.

6. The method defined in claim 4, further comprising separating contaminants from said fluid sample in said collection chamber, wherein the separating of said contaminants includes trapping said carrier elements with the coupled microbiological entity of interest in said collection chamber while flushing remaining portions of said fluid sample from said collection chamber.

7. The method defined in claim 1 wherein said microbiological entity of interest is a pathogenic strain of bacteria, further comprising measuring an electrical parameter of fluid in said collection chamber to detect metabolic activity of said microbiological entity of interest, thereby determining viability of said microbiological entity of interest.

8. The method defined in claim 1, further comprising extracting said fluid sample from a food product prior to delivering of said fluid sample to said biochip.

9. A method for collecting and rapidly concentrating a microbiological substance, comprising:
   providing a microfabricated boichip having a collection chamber;
   delivering a fluid sample to said collection chamber in said biochip, said fluid sample containing a microbiological entity of interest;
   generating a spatially non-uniform electric field in said collection chamber in a pulsed mode so that successive intervals of application of said non-uniform electric field are spaced from one another by periods of time;
   retaining said microbiological entity of interest in said collection chamber during the successive intervals of application of said non-uniform electric field, at least partially by virtue of said non-uniform electric field;
   retaining said microbiological entities of interest in said collection chamber during said periods of time, by attaching said microbiological entity of interest to at least one fixed or permanent surface of said collection chamber via antibodies disposed on said surface; and
   removing at some contaminants from said fluid sample in said collection chamber by flowing said fluid sample through and out of said chamber.

10. The method defined in claim 9, further comprising after the removing of contaminants from said fluid sample, operating detection elements in said collection chamber repeatedly over time to measure an electrical parameter of said fluid sample to detect changes in electrical impedance: of said fluid sample arising from metabolic activity of said microbiological entity of interest in said fluid sample to determine whether the fluid sample contains said microbiological entity of interest in a viable form.

11. A method for testing for he presence of a viable microorganism, comprising:
   flowing a fluid sample possibly containing a microorganism of a preselected type to a collection chamber having a volume less than approximately 1 microliter;
   at least temporarily retaining said microorganism in said collection chamber by dielectrophoresis applied in a pulsed mode so that successive intervals of application of a non-uniform electric field are spaced from one another by periods of time;
   retaining said microorganism in said collection chamber during the successive intervals of application of said non-uniform electric field and during, at least partially by virtue of said non-uniform electric field;
   retaining said microbiological entity of interest in said collection chamber during said periods of time;
   terminating the flowing of said fluid sample to said collection chamber;
   after the terminating of flow to said collection chamber, periodically making measurements of an electrical parameter of an electrical circuit incorporating said collection chamber and a fixed amount of fluid therein;

retaining said microorganism in said collection chamber during the making of said measurements; and automatically using said measurements to detect changes in electrical impedance of said fixed amount of fluid arising from metabolic activity of the microorganism, thereby determining viability of the microorganism.

12. The method defined in claim 11 wherein the preparing of said fluid sample includes attaching said microorganism to carrier elements, the retaining of said microorganism in said collection chamber includes retaining said carrier elements therein.

13. A method for testing for the presence of a viable microorganism, comprising:

delivering a fluid sample possibly containing a microorganism of a preselected type to a collection chamber having a volume less than approximately 1 microliter;

applying a dielectrophoresis field to at least temporarily retain said microorganism in said collection chamber;

periodically turning off said dielectrophoresis field;

retaining said microorganism in said collection chamber during the application of said dielectrophoresis field and when said dielectrophoresis field is turned off;

when said dielectrophoresis field is turned off, periodically making measurements of an electrical parameter of an electrical circuit incorporating said collection chamber and a fixed amount of fluid therein; and automatically using said measurements to detect changes in electrical impedance of said fixed amount of fluid arising from metabolic activity of the microorganism, thereby determining viability of the microorganism.

14. A method for testing for the presence of a viable microorganism, comprising:

flowing a fluid sample possibly containing a microorganism of a preselected type to a collection chamber having a volume less than approximately 1 microliter;

applying a dielectrophoresis field to the fluid sample in said collection chamber to at least temporarily retain said microorganism in said collection chamber;

turning off said dielectrophoresis field;

after the turning off said dielectrophoresis field, introducing a nutrient solution into said collection chamber;

retaining said microorganism in said collection chamber during application of said dielectrophoresis field and when said dielectrophoresis field is turned off;

after the introducing of said nutrient solution into said collection chamber and while said dielectrophoresis field is turned off and said microorganism is retained in said collection chamber, periodically making measurements of an electrical parameter of an electrical circuit incorporating said collection chamber and a fixed amount of nutrient containing fluid therein; and automatically using said measurements to detect changes in electrical impedance of said fixed amount of nutrient containing fluid arising from metabolic activity of the microorganism, thereby determining viability of the microorganism.

* * * * *